United States Patent
Lee et al.

(10) Patent No.: US 12,241,071 B2
(45) Date of Patent: Mar. 4, 2025

(54) COMPOSITION FOR EDITING FLAVONOID BIOSYNTHETIC GENE BY USING CRISPR/Cas9 SYSTEM, AND USE THEREOF

(71) Applicant: TOOLGEN INCORPORATED, Seoul (KR)

(72) Inventors: Geung Joo Lee, Sejong (KR); Luhua Tu, Daejeon (KR); Saminathan Subburaj, Daejeon (KR)

(73) Assignee: TOOLGEN INCORPORATED, Seoul (KR)

( * ) Notice: Subject to any disclaimer, the term of this patent is extended or adjusted under 35 U.S.C. 154(b) by 303 days.

(21) Appl. No.: 16/973,140

(22) PCT Filed: Jun. 10, 2019

(86) PCT No.: PCT/KR2019/006965
§ 371 (c)(1),
(2) Date: Dec. 8, 2020

(87) PCT Pub. No.: WO2019/235907
PCT Pub. Date: Dec. 12, 2019

(65) Prior Publication Data
US 2021/0254086 A1   Aug. 19, 2021

(30) Foreign Application Priority Data

Jun. 8, 2018 (KR) ........................ 10-2018-0065923
May 2, 2019 (KR) ........................ 10-2019-0051273

(51) Int. Cl.
C12N 15/82 (2006.01)
C12N 9/22 (2006.01)
C12N 15/113 (2010.01)

(52) U.S. Cl.
CPC ........... *C12N 15/8216* (2013.01); *C12N 9/22* (2013.01); *C12N 15/113* (2013.01)

(58) Field of Classification Search
None
See application file for complete search history.

(56) References Cited

U.S. PATENT DOCUMENTS

2019/0010471 A1   1/2019   Zhang et al.

FOREIGN PATENT DOCUMENTS

| KR | 10-2011-0045964 A | 5/2011 |
| KR | 10-2015-0145282 A | 12/2015 |
| KR | 10-1832457 B1 | 2/2018 |
| KR | 10-2018-0034404 A | 4/2018 |

OTHER PUBLICATIONS

Klimel-Chodacka, M. et al. (2018). Efficient CRISPR/Cas9-based genome editing in carrot cells. Plant Cell Report (2018). 37: 575-586.*
Nishihara et al. (2018). Application of the CRISPR/Cas9 system for modification of flower color in Torenia fournieri. BMC Plant Biology. 18:331.*
Houwelingen et al. (1998). Analysis of flower pigmentation mutants generated by random transposon mutagenesis in Petunia hybrida. The Plant Journal. 13(1):39-50.*
Obsuwan, 2003, , Characterization of Pigment and Disease resistance Genes in Dendrobium Breeding, PhD thesis, University of Hawai'i, pp. 1-149; selected pages only.*
Lee et al. (2016), Target-directed gene-editing approach for developing a new horticultural crop. Acta Hortic. 1127. ISHS 2016. DOI 10.17660/ActaHortic.2016.1127.45.*
Britsch et al (2006). Molecular cloning, sequence analysis, and in vitro expression of flavanone 3 beta-hydroxylase from Petunia hybrida. J. Biol. Chem, 267(8):5380-538.*
Klimek-Chodacka, M. et al. (2018) "Efficient CRISPR/Cas9-based genome editing in carrot cells.", *Plant Cell Reports*, 37:575-586. (Jan. 13, 2018).
International Search Report, dated Oct. 11, 2019 issued in corresponding International Patent Application No. PCT/KR2019/006965, with English translation.
Office Action from corresponding Korean Application No. 10-2020-7035219, dated Dec. 19, 2024.
Lee, G.-J., "P0011: Protoplast-Based CRISPR/Cas9 for Modification of Petunia Flower Color", Plant and Animal Genome XXVI Conference, Jan. 2018, 2 page summary.

* cited by examiner

*Primary Examiner* — Brent T Page
(74) *Attorney, Agent, or Firm* — Harness, Dickey & Pierce, P.L.C.

(57) ABSTRACT

The present application relates to a method for inducing flavonoid biosynthetic gene-editing in a cell by using a CRISPR/CAS9 system.

4 Claims, 32 Drawing Sheets
Specification includes a Sequence Listing.

FIG. 12

Target gene : F3H-A_wt
Target site : GTTAAGGCATGTGAAGATTGGGG (+)

* Result summary

| Total reads | WT | insertions | deletions | In-del frequency |
|---|---|---|---|---|
| 26,474 | 26,459 | 15 | 0 | 15(0.1%) | underline : RGEN
decline : insertion sequence
shade : mismatch sequence

* Sequence analysis data

CTGAAATATGTGACAAGATTGTTAAGGCATGTGAAGATTGGGGCGTTTTTCAAGTTGTGGATC    Target sequence Most frequent sequences

| Sequence | Type | Leads |
|---|---|---|
| CTGAAATATGTGACAAGATTGTTAAGGCATGTGAAGATTGGGGCGTTTTTCAAGTTGTGGATC | Wild-type | 26080 |
| CTGAAATATGTGACAAGATTGTTAAGGCATGTGAAGATTGGGGCGTTTTTCAAGTTGTGTGATC | Wild-type | 379 |
| CTGAAATATGTGACAAGATTGTTAAGGCATGTGAAGATTGGGGATTGGGGCGTTTTTCAAGTTGTGGATC | 1 bp insertion(Out of frame) | 15 |
| | Total | 26474 |

FIG. 13

Target gene : F3H-B_wt
Target site : GTTAAGGCATGTGAAGATTGGGG (+)

* Result summary

| Total reads | WT | insertions | deletions | In-del frequency |
|---|---|---|---|---|
| 25,327 | 25,312 | 15 | 0 | 15 (0.1%) | underline : RGEN
decline : insertion sequence
shade : mismatch sequence

* Sequence analysis data

CTGAAATATGTGACAAGATTGTTAAGGCATGTGAAGATTGGGGCGTTTTTCAAGTTGTTGATC   Target sequence

| Most frequent sequences | Type | Leads |
|---|---|---|
| CTGAAATATGTGACAAGATTGTTAAGGCATGTGAAGATTGGGGCGTTTTTCAAGTTGTTGATC | wild-type | 25105 |
| CTGAAATATGTGACAAGATTGTTAAGGCATGTGAAGATTGGGGCGTTTTTCAAGTTGTTGATC | wild-type | 207 |
| CTGAAATATGTGACAAGATTGTTAAGGCATGTGAAGATTGGGGGCGTTTTTCAAGTTGTTGATC | 1 bp insertion(Out of frame) | 15 |
| | Total | 25327 |

FIG. 14

Target gene : F3H-A_1226 P1C7
Target site : GTTAAGGCATGTGAAGATTGGGG (+)

* Result summary

| Total reads | WT | insertions | deletions | In-del frequency |
|---|---|---|---|---|
| 30,592 | 524 | 30,068 | 0 | 30,068(98.3%) |

* Sequence analysis data underline : RGEN
decline : insertion sequence
shade : mismatch sequence Target sequence
CTGAAATATGTGACAAGATTGTTAAGGCATGTGAAGATTGGGGCGTTTTTCAAGTTGTGGATC Most frequent sequences

| Sequence | Type | Leads |
|---|---|---|
| CTGAAATATGTGACAAGATTGTTAAGGCATGTGAAGATTGGGGCGTTTTTCAAGTTGTTGATC | wild-type | 286 |
| CTGAAATATGTGACAAGATTGTTAAGGCATGTGAAGATTGGGGCGTTTTTCAAGTTGTGGATC | wild-type | 238 |
| CTGAAATATGTGACAAGATTGTTAAGGCATGTGAAGATTGGGGGCGTTTTTCAAGTTGTGGATC | 1 bp insertion(Out of frame) | 30068 |
| | Total | 30592 |

FIG. 15

Target gene : F3H-B_1226 P1C7
Target site : GTTAAGGCATGTGAAGATTGGGG (+)

* Result summary

| Total reads | WT | insertions | deletions | In-del frequency |
|---|---|---|---|---|
| 29,834 | 524 | 29,310 | 0 | 29,310(98.2%) | underline : RGEN
decline : insertion sequence
shade : mismatch sequence

* Sequence analysis data

CTGAAATATGTGACAAGATTGTTAAGGCATGTGAAGATTGGGGCGTTTTTCAAGTTGTTGATC    Target sequence

| Most frequent sequences | Type | Leads |
|---|---|---|
| CTGAAATATGTGACAAGATTGTTAAGGCATGTGAAGATTGGGGCGTTTTTCAAGTTGTTGATC | Wild-type | 281 |
| CTGAAATATGTGACAAGATTGTTAAGGCATGTGAAGATTGGGGCGTTTTTCAAGTTGTGGATC | Wild-type | 243 |
| CTGAAATATGTGACAAGATTGTTAAGGCATGTGAAGATTGGGGGCGTTTTTCAAGTTGGGGATC | 1 bp insertion(Out of frame) | 29310 |
| | Total | 29834 |

FIG. 16

Target gene : F3H-A_1226 P3C5
Target site : GTTAAGGCATGTGAAGATTGGGG (+)

* Result summary

| Total reads | WT | insertions | deletions | In-del frequency |
|---|---|---|---|---|
| 22,869 | 322 | 122 | 22,425 | 22,547(98.6%) |

* Sequence analysis data

CTGAAATATGTGACAAGATTGTTAAGGCATGTGAAGATTGGGGCGTTTTCAAGTTGTGGATC underline : RGEN
decline : insertion sequence
shade : mismatch sequence Target sequence Most frequent sequences

| | Type | Reads |
|---|---|---|
| CTGAAATATGTGACAAGATTGTTAAGGCATGTGAAGATTGGGGCGTTTTCAAGTTGTGGATC | | 185 |
| CTGAAATATGTGACAAGATTGTTAAGGCATGTGAAGATTGGGGCGTTTTCAAGTTGTGGATC | wild-type | 137 |
| CTGAAATATGTGACAAGATTGTTAAGGCATGT----ATTGGGGCGTTTTCAAGTTGTGGATC | 4 bp deletion (Out of frame) | 22425 |
| CTGAAATATGTGACAAGATTGTTAAGGCATGTGAAGATTGGGGCGTTTTCAAGTTGTGGATC | 1 bp insertion(Out of frame) | 122 |
| | Total | 22869 |

FIG. 17

Target gene : F3H-B_1226 P3C5
Target site : GTTAAGGCATGTGAAGATTGGGG (+)

* Result summary

| Total reads | WT | insertions | deletions | In-del frequency |
|---|---|---|---|---|
| 22,093 | 322 | 120 | 21,651 | 21,771(98.6%) | underline : RGEN
decline : insertion sequence
shade : mismatch sequence

* Sequence analysis data

CTGAAATATGTGACAAGATTGTTAAGGCATGTGAAGATTGGGGCGTTTTCAAGTTGTTGATC    Target sequence Most frequent sequences

| Sequence | Type | Reads |
|---|---|---|
| CTGAAATATGTGACAAGATTGTTAAGGCATGTGAAGATTGGGGCGTTTTCAAGTTGTTGATC | wild-type | 216 |
| CTGAAATATGTGACAAGATTGTTAAGGCATGTGAAGATTGGGGCGTTTTCAAGTTGTTGATC | wild-type | 106 |
| CTGAAATATGTGACAAGATTGTTAAGGCATGT----ATTGGGGCGTTTTCAAGTTGTTGATC | 4 bp deletion (Out of frame) | 21651 |
| CTGAAATATGTGACAAGATTGTTAAGGCATGTGAAGATTGGGGCGTTTTCAAGTTGTTGATC | 1 bp insertion(Out of frame) | 120 |
| | Total | 22093 |

FIG. 18

Target gene : F3H-A_1226 P4C4
Target site : GTTAAGGCATGTGAAGATTGGGGG (+)

* Result summary

| Total reads | WT | insertions | deletions | In-del frequency |
|---|---|---|---|---|
| 63,419 | 264 | 63,153 | 2 | 63,155(99.6%) | underline : RGEN
decline : insertion sequence
shade : mismatch sequence

* Sequence analysis data

Target sequence
CTGAAATATGTGACAAGATTGTTAAGGCATGTGAAGATTGGGGCGTTTTTCAAGTTGTGGATC

| Most frequent sequences | Type | Leads |
|---|---|---|
| CTGAAATATGTGACAAGATTGTTAAGGCATGTGAAGATTGGGGCGTTTTTCAAGTTGTGGATC | wild-type | 256 |
| CTGAAATATGTGACAAGATTGTTAAGGCATGTGAAGATTGGGGCGTTTTTCAAGTTGTGATC | wild-type | 8 |
| CTGAAATATGTGACAAGATTGTTAAGGCATGTGAAGATTGGGGACGTTTTTCAAGTTGTGGATC | 1 bp insertion(Out of frame) | 63153 |
| CTGAAATATGTGACAAGATTGTTAAGGCATGTGAAGATT-GGCGTTTTTCAAGTTGTGGATC | 1 bp deletion (Out of frame) | 2 |
| | Total | 63419 |

FIG. 19

Target gene : F3H-B_1226 P4C4
Target site : GTTAAGGCATGTGAAGATTGGGG (+)

* Result summary

| Total reads | WT | insertions | deletions | In-del frequency |
|---|---|---|---|---|
| 61,858 | 264 | 61,592 | 2 | 61,594(99.6%) | underline : RGEN
decline : insertion sequence
shade : mismatch sequence

* Sequence analysis data

Target sequence
CTGAAATATGTGACAAGATTGTTAAGGCATGTGAAGATTGGGGCGTTTTCAAGTTGTTGATC

| Most frequent sequences | Type | reads |
|---|---|---|
| CTGAAATATGTGACAAGATTGTTAAGGCATGTGAAGATTGGGGCGTTTTCAAGTTGTTGATC | wild-type | 256 |
| CTGAAATATGTGACAAGATTGTTAAGGCATGTGAAGATTGGGGCGTTTTCAAGTTGTTGATC | wild-type | 8 |
| CTGAAATATGTGACAAGATTGTTAAGGCATGTGAAGATTGGGGGCGTTTTCAAGTTGTTGATC | 1 bp insertion(Out of frame) | 61,592 |
| CTGAAATATGTGACAAGATTGTTAAGGCATGTGAAGATT-GGGCGTTTTCAAGTTGTTGATC | 1 bp deletion (Out of frame) | 2 |
| | Total | 61858 |

FIG. 26

Target gene : F3H-A_0324 L4-1
Target site : GTTAAGGCATGTGAAGATTGGGG (+)

* Result summary

| Total reads | WT | insertions | deletions | In-del frequency |
|---|---|---|---|---|
| 42,764 | 20,814 | 21,950 | 0 | 21,950(51.3%) | underline : RGEN
decline : insertion sequence
shade : mismatch sequence

* Sequence analysis data

CTGAAATATGTGACAAGATTGTTAAGGCATGTGAAGATTGGGGCGTTTTTCAAGTTGTGGATC  Target sequence

| Most frequent sequences | Type | Leads |
|---|---|---|
| CTGAAATATGTGACAAGATTGTTAAGGCATGTGAAGATTGGGGCGTTTTTCAAGTTGTGGATC | Wild-type | 20692 |
| CTGAAATATGTGACAAGATTGTTAAGGCATGTGAAGATTGGGGCGTTTTTCAAGTTGTGGATC | Wild-type | 122 |
| CTGAAATATGTGACAAGATTGTTAAGGCATGTGAAGATTGGGGCGTTTTTCAAGTTGTGGATC | 1 bp insertion(Out of frame) | 21950 |
| | Total | 42764 |

FIG. 27

Target gene : F3H-B_0324 L4-1
Target site : GTTAAGGCATGTGAAGATTGGGG (+)

* Result summary

| Total reads | WT | insertions | deletions | In-del frequency |
|---|---|---|---|---|
| 41,276 | 20,054 | 21,222 | 0 | 21,222(51.4%) | underline : RGEN
decline : insertion sequence
shade : mismatch sequence

* Sequence analysis data

CTGAAATATGTGACAAGATTGTTAAGGCATGTGAAGATTGGGGCGTTTTTCAAGTTGTTGATC    Target sequence Most frequent sequences                                                                                 Type                              Leads
CTGAAATATGTGACAAGATTGTTAAGGCATGTGAAGATTGGGGCGTTTTTCAAGTTGTTGATC    wild-type                         19945
CTGAAATATGTGACAAGATTGTTAAGGCATGTGAAGATTGGGGCGTTTTTCAAGTTGTTGATC    wild-type                           109
CTGAAATATGTGACAAGATTGTTAAGGCATGTGAAGATTGGGGCGTTTTTCAAGTTGTTGATC    1 bp insertion(Out of frame)     21222
                                                                                                     Total  41276

FIG. 28

Target gene : F3H-A_0324 L9-1
Target site : GTTAAGGCATGTGAAGATTGGGG (+)

* Result summary

| Total reads | WT | Insertions | deletions | In-del frequency |
|---|---|---|---|---|
| 48,824 | 998 | 45,532 | 5,294 | 47,826(98%) | underline : RGEN
decline : insertion sequence
shade : mismatch sequence

* Sequence analysis data

CTGAAATATGTGACAAGATTGTTAAGGCATGTGAAGATTGGGGCGTTTTCAAGTTGTGGATC   Target sequence

| Most frequent sequences | Type | Reads |
|---|---|---|
| CTGAAATATGTGACAAGATTGTTAAGGCATGTGAAGATTGGGGCGTTTTCAAGTTGTGGATC | wild-type | 682 |
| CTGAAATATGTGACAAGATTGTTAAGGCATGTGAAGATTGGGGCGTTTTCAAGTTGTGGATC | wild-type | 316 |
| CTGAAATATGTGACAAGATTGTTAAGGCATGTGAAGATTGGGGGCGTTTTCAAGTTGTGGATC | 1 bp insertion(Out of frame) | 45532 |
| CTGAAATATGTGACAAGATTGTTAAGGCATGTGAA--ATTGGGGCGTTTTCAAGTTGTGGATC | 2 bp deletion (Out of frame) | 832 |
| CTGAAATATGTGACAAGATTGTTAAGGCATGTGA---GATTGGGGCGTTTTCAAGTTGTGGATC | 3 bp deletion (In frame) | 669 |
| CTGAAATATGTGACAAGATTGTTAAGGCATGT----GATTGGGGCGTTTTCAAGTTGTGGATC | 1 bp deletion (Out of frame) | 539 |
| CTGAAATATGTGACAAGATTGTTAAGGCATGT-----ATTGGGGCGTTTTCAAGTTGTGGATC | 5 bp deletion (Out of frame) | 368 |
| CTGAAATATGTGACAAGATTGTTAAGGC--------ATTGGGGCGTTTTCAAGTTGTGGATC | 8 bp deletion (Out of frame) | 342 |
| ---------------------------------------------------------TTGTGGATC | 97 bp deletion (In frame) | 123 |
| CTGAAATATGTGACAAGA----------------------------TTGTGGATC | 93 bp deletion (In frame) | 160 |
| CTGAAATATGTGACAAGATTGTTAAGGCATGTG-------------TTGTGGATC | 36 bp deletion (In frame) | 141 |
| CTGAAATATGTGACAAGATTG----CGTTTTCAAGTTGTGGATC | 4 bp deletion (Out of frame) | 257 |
| CTGAAATATGTGACAAGATTG----------------TTGGGGCGTTTTCAAGTTGTGGATC | 16 bp deletion (Out of frame) | 152 |
| | Total | 48824 |

FIG. 30

Target gene : F3H-A_0324 L9-2
Target site : GTTAAGGCATGTGAAGATTGGGG (+)

* Result summary

| Total reads | WT | insertions | deletions | In-del frequency |
|---|---|---|---|---|
| 59,463 | 93 | 57,317 | 1,999 | 59,370(99.8%) | underline : RGEN
decline : insertion sequence
shade : mismatch sequence

Target sequence

* Sequence analysis data

CTGAAATATGTGACAAGATTGTTAAGGCATGTGAAGATTGGGGCGTTTTTCAAGTTGTGGATC

| Most frequent sequences | Type | Leads |
|---|---|---|
| CTGAAATATGTGACAAGATTGTTAAGGCATGTGAAGATTGGGGCGTTTTTCAAGTTGTGGATC | wild-type | 93 |
| CTGAAATATGTGACAAGATTGTTAAGGCATGTGAAGATTGGGGATTTTTCAAGTTGTGGAT | 1 bp insertion(Out of frame) | 57227 |
| CTGAAATATGTGACAAGATTGTTAAGGCATGTGAAGATTGGGG--CGTTTTTCAAGTTGTGGATC | 2 bp deletion (Out of frame) | 1562 |
| CTGAAATATGTGACAAGATTGTTAAGGCATGTGA--ATTGGGGCGTTTTTCAAGTTGTGGATC | 1 bp deletion (Out of frame) | 69 |
| CTGAAATATGTGACAAGATTGTTAAGGCATGTGAA-TTTGGGGCGTTTTTCAAGTTGTGGATC | 1 bp deletion (Out of frame) | 65 |
| CTGAAATATGTGACAAGATTGTTAAGGCATGT-----TTTGGGGCGTTTTTCAAGTTGTGGATC | 4 bp deletion (Out of frame) | 51 |
| ------------------------------------------------------------- | 83 bp deletion (Out of frame) | 40 |
| CTGAAATATGTGACAAGATTGTTAAGGCATGTGAAGAATTGGGGCGTTTTTCAAGTTGTGGA | 2 bp insertion(Out of frame) | 40 |
| | Total | 59463 |

FIG. 31

Target gene : F3H-B_0324 L9-2
Target site : GTTAAGGCATGTGAAGATTGGGG (+)

* Result summary

| Total reads | WT | Insertions | Deletions | In-del frequency |
|---|---|---|---|---|
| 58,119 | 179 | 55,992 | 1,948 | 57,940(99.7%) | underline : RGEN
decline : insertion sequence
shade : mismatch sequence
Target sequence

* Sequence analysis data

| Sequence | Type | Reads |
|---|---|---|
| CTGAAATATGTGACAAGATTGTTAAGGCATGTGAAGATTGGGGCGTTTTTCAAGTTGTGATC | | |
| CTGAAATATGTGACAAGATTGTTAAGGCATGTGAAGATTGGGGCGTTTTTCAAGTTGTGATC | wild-type | 123 |
| CTGAAATATGTGACAAGATTGTTAAGGCATGTGAAGATTGGGGCGTTTTTCAAGTTGTGATC | wild-type | 56 |
| CTGAAATATGTGACAAGATTGTTAAGGCATGTGAAGATTGGGGAGTTTTTCAAGTTGTGGAT | 1 bp insertion(Out of frame) | 55848 |
| CTGAAATATGTGACAAGATTGTTAAGGCATGTGA--ATTGGGGCGTTTTTCAAGTTGTGATC | 2 bp deletion (Out of frame) | 1562 |
| CTGAAATATGTGACAAGATTGTTAAGGCATGTGAAGATTTGGGGCGTTTTTCAAGTTGTGGA | 2 bp insertion(Out of frame) | 144 |
| CTGAAATATGTGACAAGATTGTTAAGGCATGTGAA-TTTGGGGCGTTTTTCAAGTTGTGATC | 1 bp deletion (Out of frame) | 69 |
| CTGAAATATGTGACAAGATTGTTAAGGCATGT----TTTGGGGCGTTTTTCAAGTTGTGATC | 4 bp deletion (Out of frame) | 65 |
| | 66 bp deletion (Out of frame) | 18 |
| | Total | 58119 |

Most frequent sequences

COMPOSITION FOR EDITING FLAVONOID BIOSYNTHETIC GENE BY USING CRISPR/Cas9 SYSTEM, AND USE THEREOF

CROSS-REFERENCE TO RELATED APPLICATIONS

This application is a national phase application of PCT Application No. PCT/KR2019/006965, filed on Jun. 10, 2019, which claims priority to Korean Patent Application No. 10-2019-0051273, filed on May 2, 2019 and Korean Patent Application No. 10-2018-0065923, filed on Jun. 8, 2018. The entire disclosure of the applications identified in this paragraph is incorporated herein by references.

FIELD

The present application relates to a composition for editing a flavonoid biosynthetic gene using a CRISPR/CAS9 system, and a use thereof.

BACKGROUND

As a gene scissors technology (engineered nucleases technology), after first-generation zinc-finger nuclease (ZFN) and the second-generation TALEN, a ribonucleoprotein complex (RNP), which is third-generation gene scissors technology, capable of targeting only a desired gene in not only animals, but also plant cells using a CRISPR/Cas system functioning in bacteria or archaea was reported in 2013.

Unlike the existing ZFN and TALEN, the RNP has big advantages in that a protein need not be produced according to DNA to be cleaved and a desired gene can be edited by changing only a guide RNA using only one protein, and is a DNA-free non-GMO variety breeding technology unlike the existing GMO technologies, and recently, the US USDA has announced that it would allow plant breeding by gene editing such as CRISPR and would not regulate plant breeding by gene editing unlike existing GMOs, and the Food Standards Australia New Zealand has announced that new technology crops with simple gene deletion are not regarded as GMOs.

Targeted genome editing (TGE) using gene scissors (the engineered nucleases (EN)) has been shown to modify the properties of various food crops such as wheat, corn, rice and beans. More recently, one of the gene scissors, such as CRISPR/Cas9 technology, has also been successfully applied to Solanaceae crops including tomatoes and potatoes. A protoplast transient expression system using CRISPR/Cas9 has been adopted as a multipurpose method for genome editing of various plants.

The present inventors have developed and standardized an efficient protocol for a transient expression system of a CRISPR/Cas9 RNP for Petunia×hybrida. In the present application, it was confirmed that in order to produce a DNA-free gene-edited flavonoid biosynthesis-involved gene mutant in an ornamental plant, flower colors were changed by mutating the flavone 3-hydroxylase (F3H) gene based on CRISPR/Cas9 in petunia protoplasts, thereby completing the present invention.

SUMMARY

Technical Problem

The present application was derived from the above requirements, and the present applicants have separated and extracted the protoplasts of Petunia, and then transduced a complex (ribonucleoprotein (RNP)) of a guide RNA targeting a sequence of a flavone 3-hydroxylase (F3H) gene and a Cas9 protein into the extracted protoplasts. Thereafter, when wild-type and transduced protoplasts were used, and as a result of the analysis of high resolution melting (HRM) and targeted deep sequencing of an F3H position, it could be observed that an insertion/deletion (InDel) mutation occurred at the target sequence position of the F3H gene, and it was confirmed that a flower color change occurred in a plant differentiated from the protoplast in which the mutation was induced, thereby completing the present application.

Technical Solution

In order to solve the above problem, the present application provides a composition comprising:
a guide RNA capable of forming complementary bonds with a target sequence in genomic sequence of a factor involved synthesis of anthocyanin-type flavonoids on genomic DNA in a plant, or a nucleic acid sequence encoding the same; and
a Cas protein capable of forming a complex with the guide RNA to cleave the genomic sequence of a factor, or a nucleic acid sequence encoding the same,
wherein the nucleic acid encoding the guide RNA has a sequence which is the same as or complementary with the target sequence adjacent to a PAM sequence recognized by the Cas protein, and
wherein the composition induces an artificial mutation in the genomic sequence of the factor involved synthesis of anthocyanin-type flavonoids on genomic DNA in a plant, and changes the color characteristics of one or more selected from the group consisting of a flower, a seed, a fruit and a leaf of a plant.

In addition, in order to solve the above problems, the present application provides method of producing a transgenic plant, which includes:
introducing a composition comprising a guide RNA which is capable of forming complementary bonds with a target sequence in genomic sequence of a factor involved synthesis of anthocyanin-type flavonoids on genomic DNA in a plant cell, or a nucleic acid sequence encoding the same; and a Cas protein, which forms a complex with the guide RNA to cleave genomic sequence of the factor, or a nucleic acid sequence encoding the same into protoplasts; and
regenerating the protoplasts,
wherein the regenerated protoplasts comprise an artificial mutation in genomic sequence of a factor involved synthesis of anthocyanin-type flavonoids on genomic DNA,
wherein the factor involved synthesis of anthocyanin-type flavonoids is a gene of one or more selected from F3H, F3'H and F3'5'H, and
wherein the plant has a changed color characteristics compared to a wild type.

Advantageous Effects

The gene editing method of the present application does not have an exogenous gene inserted and has only small mutations which are indistinguishable from natural mutations, and thus is expected to save money and time unlike GMO crops which require enormous costs and time to evaluate safety and environmental hazards. In addition, the method of the present application is an improved transient expression system, and can effectively change the flower colors of crops as well as the colors of seeds, fruits, and various plant organs without using a traditional transgenic method, and thus can be usefully used for color correction for ornamental and functional purposes in the field of horticulture.

BRIEF DESCRIPTION OF THE DRAWINGS

FIGS. 12 and 13 illustrate the results of sequencing analysis and indel of petunias in which wild-type F3Ha and F3Hb (named F3H-A_wt and F3H-B_wt, respectively) have undergone RNP-mediated transformation.

FIGS. 14, 15, 16, 17, 18 and 19 illustrate the results of sequencing analysis and indel of petunias in which mutant F3Ha and F3Hb (named F3H-A_1226P1C7, F3H-B_1226P1C7, F3H-A_1226P3C5, F3H-B_1226P3C5, F3H-A_1226P4C4, and F3H-B_1226P4C4, respectively) have undergone RNP-mediated transformation.

FIGS. 26, 27, 28, 29, 30, and 31 illustrate the results of sequencing analysis and indel of petunias in which mutant F3Ha and F3Hb (named F3H-A_0324L4-1, F3H-B_0324L4-1, F3H-A_0324L9-1, F3H-B_0324L9-1, F3H-A_0324L9-2, and F3H-B_0324L9-2, respectively) have undergone agrobacterium-mediated transformation.

DETAILED DESCRIPTION

Figure 1:
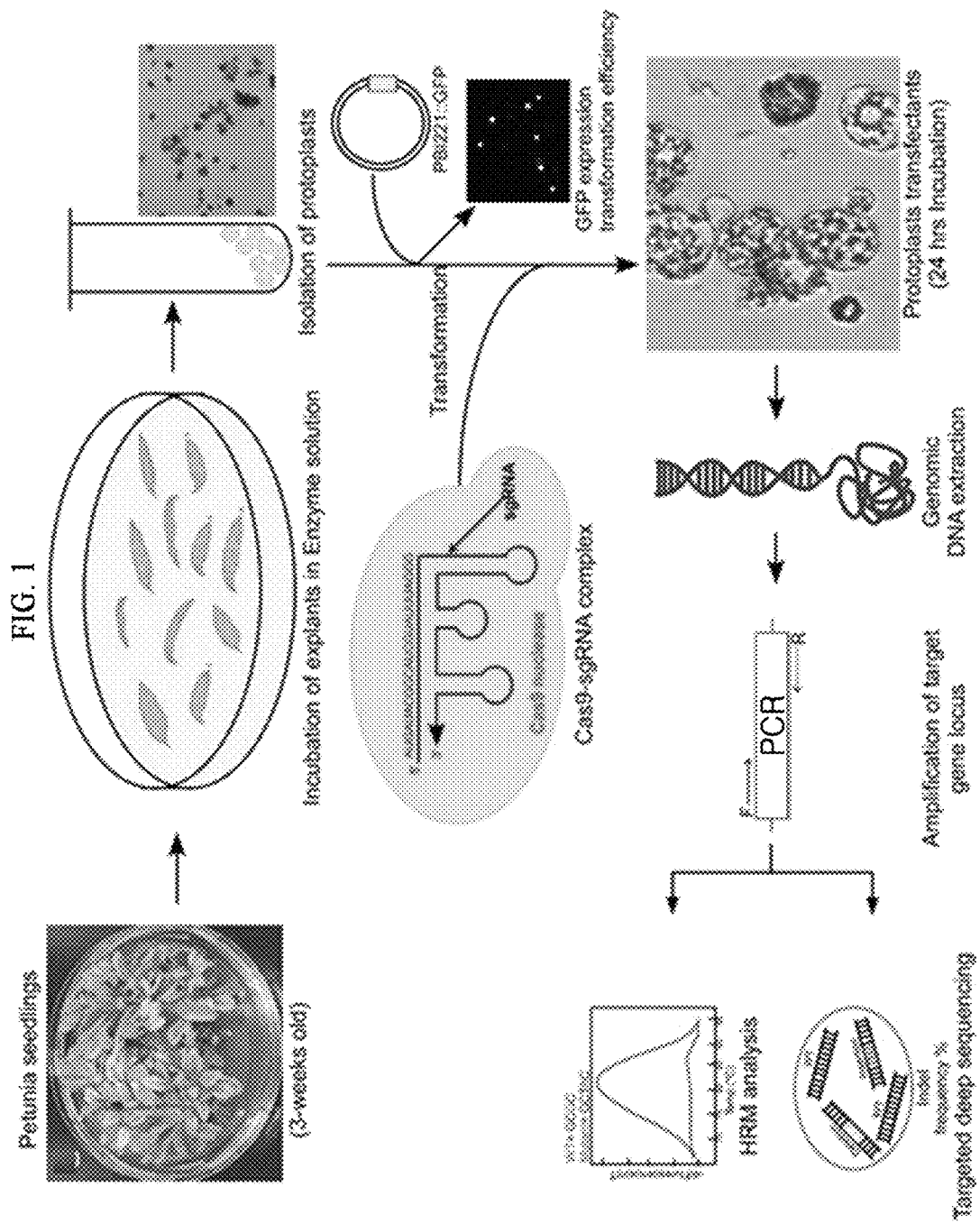
FIG. 1 illustrates the processes of extracting *petunia* protoplasts and inducing genome-edited cells using the CRISPR/Cas9 system.

The present application relates to a method for regulating the expression of an F3H gene in a plant, and a composition used therein.

The F3H gene affects the formation of various anthocyanin pigments in plants. The F3H gene is a major gene for synthesizing naringenin, leucoanthocyanidins, anthocyanidins, and the like, and naringenin is involved in the production of anthocyanin pigments by conversion into dihydroflavonols.

The composition may affect the formation of anthocyanin pigments at various sites such as a seed, a fruit, a flower, a stem and a leaf of the plant.

For example, the composition may affect the formation of anthocyanin pigments at one or more sites selected from a seed, a fruit, a flower, a stem and a leaf of the plant.

As any exemplary embodiment, the composition may regulate the expression of the F3H gene in a plant to change the color of one or more sites selected from a seed, a fruit, a flower, a stem and a leaf of the plant.

As used herein, the F3H gene is a term which includes both an F3'H gene and an F3'5'H gene.

A plant having the F3H gene may be a plant belonging to Solanaceae crops, *Rosaceae*, and *Asteraceae*, but is not limited thereto.

A plant belonging to *Solanaceae* crops may be, for example, eggplant, mandrake, potato, tobacco, tomato, petunia, and the like, but is not limited thereto.

A plant belonging to *Rosaceae* may be rose, white plums, Japanese kerria, and cherry tree, but is not limited thereto.

A plant belonging to *Asteraceae* may be chrysanthemum, Inula, fleabane, dandelion, and the like, but is not limited thereto.

As a specific example, the plant may be petunia, rose, chrysanthemum, and the like, but is not limited thereto.

In one aspect, the present specification provides a method for regulating the expression of the F3H gene in a plant.

The present specification provides a method for changing color characteristics of a plant using the method for regulating the expression of the F3H gene.

As an example, the present specification provides a method for producing a plant having a color variation trait, the method including:

artificially editing a genome by introducing a composition including a guide RNA specific for a target sequence of a flavone 3-hydroxylase (F3H) gene or a nucleic acid sequence encoding the same, and an endonuclease protein or a nucleic acid sequence encoding the same into target plant cells; and regenerating a plant from the target plant cells whose genome is edited.

For example, the method may be carried out in the form of a complex of a guide RNA specific for a target sequence of a flavone 3-hydroxylase (F3H) gene and an endonuclease protein. As another example, the method may be carried out in the form of a vector including a nucleic acid sequence encoding a guide RNA specific for a target sequence of a flavone 3-hydroxylase (F3H) gene and a nucleic acid sequence encoding an endonuclease protein.

As a specific example, the present specification provides a method for producing petunia plant having a color variation trait, the method including:

artificially editing a genome by introducing a composition including a guide RNA specific for a target sequence of petunia (petunia×hybrida)-derived flavone 3-hydroxylase (F3H) gene or a nucleic acid sequence encoding the same, and an endonuclease protein or a nucleic acid sequence encoding the same into petunia plant cells; and regenerating petunia plant from the petunia plant cells whose genome is edited.

As used herein, the term "genome editing" refer to a technology capable of introducing or inducing target-directed mutations in the genome sequence of animal and plant cells including human cells. It refers to the technology capable of knocking out or knocking in a specific gene by deletion, insertion, substitution, and the like of one or more nucleic acid molecules by DNA cleavage, or introducing a mutation into a non-coding DNA sequence that does not produce a protein. For the purposes of the present application, the genome editing may be introducing a mutation into a plant, particularly using a Cas9 protein and a guide RNA. The term genome editing may be used interchangeably with the term "gene editing".

Further, the term "target gene" or "target genome" means some DNA in the genome of a plant to be edited throughout the present application. That is, in principle, the term is not limited to the type of gene, and may include all coding regions and non-coding regions. Those skilled in the art may select the target gene according to the desired mutation in the genome-edited plant to be produced according to the purpose.

The target gene may be a gene involved synthesis of anthocyanin-type flavonoids.

The gene involved synthesis of anthocyanin-type flavonoids may be flavone 3-hydroxylase (F3H), flavone 3'-hydroxylase (F3'H), flavonoid 3',5'-hydroxylase (F3'5'H), and the like, but is not limited thereto. The above F3H, F3'H, F3'5'H and the like may be associated with the formation of pigments of a flower, a fruit, and the like.

In the production method according to an exemplary embodiment of the present application, the target gene may be petunia (petunia×hybrida)-derived flavone 3-hydroxylase (F3H) gene, preferably the target gene including a sequence of SEQ ID NO: 36, but is not limited thereto.

In an exemplary embodiment of the present application, the plant genome may have the F3H gene.

The F3H gene may be one or more selected from wild type or mutant type. For example, the mutant type may have a single nucleotide polymorphism (SNP).

In a specific exemplary embodiment, the plant genome in the present application may have a wild-type F3H gene.

In a specific exemplary embodiment, the plant genome in the present application may have a mutant gene having a F3H SNP.

For example, the mutant gene having a F3H SNP may be one or more selected from SEQ ID NOs: 52 and 53.

As used herein, the term "guide RNA" refers to RNA specific for DNA encoding a sequence of a target gene, and means a ribonucleic acid that serves to lead an endonuclease protein to the target DNA sequence by binding all or part of the target DNA sequence complementarily.

The guide RNA may be a form of a dual RNA including two RNAs, that is, CRISPR RNA (crRNA) and trans-activating crRNA (tracrRNA) as constituent elements; or a form of a single-chain guide RNA (sgRNA) comprising a first portion including a sequence partially or wholly complementary to the sequence of the target DNA and a second portion including a sequence interacting with an RNA-guided nuclease, which may be included in the scope of the present application as long as the RNA-guided nuclease is in a form capable of having activity in a target sequence. The guide RNA according to the present application may be in the form of a single-strand guide RNA, but is not limited thereto, and may be appropriately selected according to the technique known in the art for the type of endonuclease used or the endonuclease-derived microorganism, and the like.

Further, the guide RNA may be a transcribed guide RNA from a plasmid template or in vitro transcribed guide RNA (for example, an oligonucleotide double strand), but is not limited thereto.

In the production method according to an exemplary embodiment of the present application, the guide RNA is specifically devised for a target sequence of a F3H gene, and the target sequence of the F3H gene may be one or more selected from the group consisting of, for example, sequences of SEQ ID NO: 1 to 5. As an exemplary embodiment, the target sequence of the F3H gene may include a sequence of SEQ ID NO: 2, but is not limited thereto. In addition, as another exemplary embodiment, the target sequence of the F3H gene may be one or more selected from the group consisting of SEQ ID NOs: 37 to 41. In addition, as another exemplary embodiment, the target sequence of the F3H gene may be one or more selected from the group consisting of SEQ ID NOs: 49 to 50.

For the SEQ ID Nos: 1 to 5 as the target sequence, the guide RNA may be one or more selected from SEQ ID NOs: 42 to 46.

For the SEQ ID Nos: 37 to 41 as target sequence, the guide RNA may be one or more selected from SEQ ID NOs: 47 to 51.

For the SEQ ID Nos: 54 and 55 as target sequence, the guide RNA may be one or more selected from SEQ ID NOs: 56 and 57.

For the SEQ ID Nos: 58 and 59 as target sequence, the guide RNA may be one or more selected from SEQ ID NOs: 60 and 61.

In the production method according to an exemplary embodiment of the present application, the endonuclease protein may be one or more selected from the group consisting of a CRISPR associated protein 9 (Cas9), a CRISPR from Prevotella and Francisella 1 (Cpf1), a transcription activator-like effector nuclease (TALEN), a zinc finger nuclease (ZFN) or as a functional analogues thereof, preferably a Cas8 protein, but is not limited thereto.

The Cas9 protein or gene information may be obtained from publicly-known databases such as GenBank of the National Center for Biotechnology Information (NCBI). For example, the Cas9 protein may be one or more selected from the group consisting of a *Streptococcus pyogenes*-derived Cas9 protein, a *Campylobacter jejuni*-derived Cas9 protein, a *Streptococcus thermophilus* or *Streptocuccus aureus*-derived Cas9 protein, a *Neisseria meningitidis*-derived Cas9 protein, a *Pasteurella multocida*-derived Cas9 protein, a *Francisella novicida*-derived Cas9 protein, and the like, but is not limited thereto.

The Cas9 protein is an RNA-guided DNA endonuclease enzyme that induces a double stranded DNA break. In order for the Cas9 protein to accurately bind to the sequence of the target DNA, thereby cleaving a DNA strand, a short sequence including three bases known as a protospacer adjacent motif (PAM) should be present next to the sequence of the target DNA, and the Cas9 protein is cleaved by estimating a position between the 3rd and 4th base pairs from a PAM sequence (NGG).

In the production method according to an exemplary embodiment of the present application, the guide RNA and the endonuclease protein form a ribonucleoprotein complex to act as a RNA-guided engineered nuclease (RGEN).

Since a plant produced by the production method of the present invention does not temporarily regulate the expression of the F3H gene but regulates the expression of the genomic DNA of the F3H gene, there is an advantage in that the regulation of the expression of the F3H gene is permanent.

The CRISPR/Cas9 system used in the present application is a genome editing method by a non-homologous end joining (NHEJ) mechanism which induces an insertion-deletion (InDel) mutation by an incomplete repair induced during the DNA repair process by introducing a double helix cleavage into a specific position of a specific gene to be edited.

In the production method according to an exemplary embodiment of the present application, the guide RNA and the endonuclease protein may be transduced directly into host cells in the form of a ribonucleoprotein complex, or may be produced in the form of a recombinant vector including DNA encoding the guide RNA and a nucleic acid sequence encoding the endonuclease protein and transduced into host cells, but the method is not limited thereto.

In the production method according to the present application, the method for transducing a complex of the guide RNA and the endonuclease protein into plant cells may be suitably selected from a calcium/polyethylene glycol method for protoplasts (Krens et al., 1982, Nature 296:72-74; Negrutiu et al., 1987, Plant Mol. Biol. 8:363-373), an electroporation method of protoplasts (Shillito et al., 1985, Bio/Technol. 3:1099-1102), microinjection into plant elements (Crossway et al., 1986, Mol. Gen. Genet. 202:179-185), (DNA or RNA-coated) particle bombardment of various plant elements (Klein et al., 1987, Nature 327:70), infection by (non-integrative) viruses in *Agrobacterium tumefaciens*-mediated gene transfer (EP 0 301 316), and the like.

The "plant cells" may be any plant cells. The plant cells may include plant cells derived from a certain site of the plant, for example, a root, a stem, a leaf, a flower, a seed, and the like. In addition, the plant cells include cultured cells, cultured tissues, and cultured organs, and the plant cells also include a tissue of a differentiated or undifferentiated plant, for example, being not limited to, root, stem, leaf, pollen, seed and various forms of cells used for the same, that is, single cells, protoplasts, bud and callus tissues. The "plant" means an entire plant including the plant cells.

For example, the plant cells of the present application may be protoplasts.

Further, as another example, the plant cells of the present application may be leaf-derived plant cells.

In the production method of the present application, any method publicly-known in the art may be used as a method for regenerating a genome-edited plant from genome-edited plant cells. Genome-edited plant cells should be regenerated into a whole plant. Techniques for the regeneration of mature plants from callus or protoplast cultures are well known in the art for many different species (Handbook of Plant Cell Culture, 1-5 volume, 1983-1989 Momillan, N.Y.).

Another aspect of the present application relates to a composition which changes the color of a plant.

The composition may be used for changing the color of a plant site, for example, a seed, a fruit, a flower, a leaf, and a stem.

The composition may be an expression-regulating composition, which may regulate the expression of a factor involved synthesis of anthocyanin-type flavonoids.

The factor involved synthesis of anthocyanin-type flavonoids may be flavone 3-hydroxylase (F3H), flavonoid 3'-hydroxylase (F3'H), flavonoid 3',5'-hydroxylase (F3'5'H), and the like, but is not limited thereto.

In particular, the present composition changes the flower color of a plant by regulating the synthesis of anthocyanin-based flavonoids involved the expression of the F3H gene.

The composition regulates the expression of a factor involved synthesis of anthocyanin-type flavonoids by editing a DNA sequence of the corresponding factor on genomic DNA present in a plant.

Such gene editing means introducing an artificial mutation into a sequence encoding the factor involved the synthesis of anthocyanin-type flavonoids in plant genomic DNA. The artificial mutation includes a mutation in which one or more nucleic acids are inserted, deleted, substituted, or inverted in a part or entire region of the genomic sequence of a wild-type gene.

For example, in the present application, the composition may decrease or increase the expression of a factor involved synthesis of anthocyanin-type flavonoids by deleting some of the DNA sequence of the corresponding factor present in a plant.

For example, in the present application, the composition may decrease or increase the expression of a factor involved synthesis of anthocyanin-type flavonoids by inserting an exogenous DNA sequence into the corresponding factor present in a plant.

For example, in the present application, the composition may decrease or increase the expression of a factor involved synthesis of anthocyanin-type flavonoids by forming an indel in a DNA sequence of the corresponding factor present in a plant.

For example, in the present application, the composition may decrease or increase the expression of a factor involved synthesis of anthocyanin-type flavonoids by substituting some of the DNA sequence of the corresponding factor present in a plant.

For example, in the present application, the composition may decrease or increase the expression of a factor involved synthesis of anthocyanin-type flavonoids by inverting some of the DNA sequence of the corresponding factor present in a plant.

The artificial mutation may be introduced into a plant genome using an engineered nuclease.

For example, the engineered nuclease may include zinc-finger nucleases (ZFNs), transcription activator-like effector nucleases (TALENs), clustered regularly interspaced short palindromic repeats/CRISPR-associated sequences (CRISPR/Cas), and the like, but is not limited thereto as long as the engineered nuclease is a technique capable of editing a target site of a gene using an artificial enzyme which is used to cleave a specific DNA site.

As a specific example, the expression-regulating composition of the present application may be a composition using CRISPR Cas.

In an exemplary embodiment of the present specification, the expression-regulating composition may include:
- at least one of a guide RNA or a nucleic acid sequence encoding the same, which is capable of binding complementarily to with a target sequence in a nucleic acid sequence of a factor involved synthesis of anthocyanin-type flavonoids; and
- at least one of a Cas protein or a nucleic acid sequence encoding the same, which is capable of cleaving or modifying a targeting site among nucleic acid sequences of the factor involved synthesis of anthocyanin-type flavonoids.

For example, in the present application, the expression-regulating composition may include:
- at least one of a guide RNA or a nucleic acid sequence encoding the same, which is capable of binding complementarily to with a target sequence in one or more nucleic acid sequences selected from F3H, F3'H, and F3'5; and
- at least one of a Cas protein or a nucleic acid sequence encoding the same, which is capable of cleaving or modifying a targeting site among one or more nucleic acid sequences selected from the F3H, F3'H, and F3'5'H.

In an exemplary embodiment, the expression-regulating composition may include:
- a guide RNA which is capable of binding complementarily to with a target sequence in one or more nucleic acid sequences selected from F3H, F3'H, and F3'5'H; and
- a Cas protein which is capable of cleaving or modifying a targeting site among nucleic acid sequences of a factor involved synthesis of anthocyanin-type flavonoids by forming a complex with the guide RNA. That is, the expression-regulating composition may be a composition in the form of a ribonucleoprotein (RNP).

The guide RNA may bind complementarily to a target sequence of a factor involved synthesis of anthocyanin-type flavonoids.

The target sequence is a sequence present in the target gene or nucleic acid, and has complementarity with the sequence of the guide RNA. In addition, the target sequence has a double strand of the target gene or nucleic acid, and thus may be a part or all of the double strand.

The target sequence can be a nucleic acid sequence of an exon and intron of a factor involved synthesis of anthocyanin-type flavonoids, or a combination thereof. For example, the guide RNA may bind complementarily to an exon of F3H.

For example, the guide RNA may bind complementarily to an exon of F3'H.

For example, the guide RNA may bind complementarily to an exon of F3'5'H.

The target sequence may be variously selected based on a PAM sequence at a step of designing a guide nucleic acid.

For example, a guide nucleic acid which is capable of forming complementary bonds with a target region of a gene may be designed by collecting sequence data of the gene using a database (for example, NCBI, and the like) of a sequence of a target nucleic acid or gene to find a site having a PAM sequence (for example, 5'-NGG-3') among the sequences, and selecting a sequence of about 20 bp from the PAM sequence.

The "protospacer-adjacent motif (PAM) sequence" is a nucleotide sequence which a Cas protein can recognize. The PAM sequences may differ depending on the origin of Cas.

For example, the PAM sequence may be one or more of the following sequences (described in a direction from 5' to 3').
- NGG (N is A, T, C or G);
- NNNNRYAC (each N is independently A, T, C or G, R is A or G, and Y is C or T);
- NNAGAAW (each N is independently A, T, C or G, and W is A or T);
- NNNNGATT (each N is independently A, T, C or G);
- NNGRR (T) (each N is independently A, T, C or G, and R is A or G); and
- TTN (N is A, T, C or G).

The guide RNA may be a dual guide RNA including crRNA (CRISPR RNA) and/or tracrRNA (trans-activating crRNA), respectively, or a single-chain guide RNA (sgRNA) in which specific sites of the crRNA and the tracrRNA are fused.

In the present specification, the Cas protein may be Cas9 or Cpf1.

The Cas9 may be Cas9 derived from various microorganisms such as *Streptococcus pyogenes*, *Streptococcus thermophilus*, *Streptococcus* sp., *Staphylococcus aureus*, *Nocardiopsis dassonvillei*, *Streptomyces pristinaespiralis*, *Streptomyces viridochromogenes*, *Streptomyces viridochromogenes*, *Streptosporangium roseum*, *Streptosporangium roseum*, *AlicyclobacHlus acidocaldarius*, *Bacillus pseudomycoides*, *Bacillus selenitireducens*, *Exiguobacterium sibiricum*, *Lactobacillus delbrueckii*, *Lactobacillus salivarius*, *Microscilla marina*, *Burkholderiales bacterium*, *Polaromonas naphthalenivorans*, *Polaromonas* sp., *Crocosphaera watsonii*, *Cyanothece* sp., *Microcystis aeruginosa*, *Synechococcus* sp., *Acetohalobium arabaticum*, *Ammonifex degensii*, *Caldicelulosiruptor bescii*, *Candidatus Desulforudis*, *Clostridium botulinum*, *Clostridium difficile*, *Finegoldia magna*, *Natranaerobius thermophilus*, *Pelotomaculum thermopropionicum*, *Acidithiobacillus caldus*, *Acidithiobacillus ferrooxidans*, *Allochromatium vinosum*, *Marinobacter* sp., *Nitrosococcus halophilus*, *Nitrosococcus watsoni*, *Pseudoalteromonas haloplanktis*, *Ktedonobacter racemifer*, *Methanohalobium evestigatum*, *Anabaena variabilis*, *Nodularia spumigena*, *Nostoc* sp., *Arthrospira maxima*, *Arthrospira platensis*, *Arthrospira* sp., *Lyngbya* sp., *Microcoleus chthonoplastes*, *Oscillatoria* sp., *Petrotoga mobilis*, *Thermosipho africanus*, or *Acaryochloris marina*. In an exemplary embodiment, a Cas9 protein derived from *Streptococcus pyogenes* may be used.

Furthermore, the Cpf1 may be Cpf1 derived from *Streptococcus*, *Campylobacter*, *Nitratifractor*, *Staphylococcus*, *Parvibaculum*, *Roseburia*, *Neisseria*, *Gluconacetobacter*, *Azospirillum*, *Sphaerochaeta*, *Lactobacillus*, *Eubacterium*, *Corynebacter*, *Carnobacterium*, *Rhodobacter*, *Listeria*, *Paludibacter*, *Clostridium*, *Lachnospiraceae*, *Clostridiaridium*, *Leptotrichia*, *Francisella*, *Legionella*, *Alicyclobacillus*, *Methanomethyophilus*, *Porphyromonas*, *Prevotella*, *Bacteroidetes*, *Helcococcus*, *Letospira*, *Desulfovibrio*, *Desulfonatronum*, *Opitutaceae*, *Tuberibacillus*, *Bacillus*, *Brevibacilus*, *Methylobacterium*, or *Acidaminococcus*.

In an exemplary embodiment of the present application, the Cas9 may be spCas9 derived from *Streptococcus pyogenes*.

When the spCas9 is used,
as a specific exemplary embodiment, the target sequence may be one or more selected from SEQ ID NO: 1 to 5. In this case, the RNA may be one or more selected from SEQ ID NOs: 42 to 46.

As another specific exemplary embodiment, the target sequence may be one or more selected from SEQ ID NOs: 37 to 41. In this case, the guide RNA may be one or more selected from SEQ ID NOs: 47 to 51.

As still another specific exemplary embodiment, the target sequence may be one or more selected from SEQ ID NOs: 54 and 55. In this case, the RNA may be one or more selected from SEQ ID NOs: 56 to 57.

As yet another specific exemplary embodiment, the target sequence may be one or more selected from SEQ ID NOs: 58 and 59. In this case, the RNA may be one or more selected from SEQ ID NOs: 60 to 61.

In the present specification, the expression-regulating composition may be provided in the form of a vector.

The vector includes a non-viral vector and a viral vector.

The viral vector may be an adenoviral vector, a retroviral vector, a binary vector, a lentiviral vector, an adeno-associated viral (AAV) vector, a vaccinia viral vector, a poxviral vector, herpes simplex virus, and the like, but is not limited thereto. The non-viral vector may be a plasmid, naked DNA, a liposome, and the like, but is not limited thereto.

Further, the expression-regulating composition may be provided to plant cells by various methods capable of carrying a gene.

For example, the method may include methods such as electroporation, a gene gun method, sonoporation, magnetofection, a polyethylene glycol (PEG) method, an *Agrobacterium* method, transient cell compression or squeezing, lipid-mediated transfection, nanoparticles, and silica.

The expression-regulating composition may be used to regulate factors involved synthesis of anthocyanin-type flavonoids by editing these factors on genomic DNA in a plant.

The editing may be one or more selected from knock-out, knock-in, and knock-down. For example, the color of a plant, for example, the flower color, may be changed by suppressing (or reducing or non-activating) or promoting (or enhancing or activating) the expression of a factor involved synthesis of flavonoids.

Such a composition of the present application and a method using the same have the following advantages.

When compared to a technique of changing the flower color using RNAi in the related art, the RNAi is used as a means for regulating post transcriptional gene expression, and does not substantially change the sequence of a genome. Therefore, when the transcription amount of the factors in the plant varies due to the effects of the environment, and the like, there is a disadvantage in that it is difficult to maintain the consistency of color expression, and it is highly likely that an unintended phenotype occurs due to the occurrence of a continuous off-target effect. In particular, with regard to the change in color of a flower, the flower is classified as a GMO because the integration of foreign genes is essential, and there are restrictions on commercialization.

In contrast, when the composition of the present application is used, an artificial mutation is directly formed in a sequence encoding a factor involved synthesis of anthocyanin-type flavonoids, for example, flavone 3-hydroxylase (F3H), flavone 3'-hydroxylase (F3'H), and flavonoid 3',5'-hydroxylase (F3'5'H) on genomic DNA of a plant, so that the expression of these factors may be permanently regulated. Therefore, a phenotype with changed color characteristics of a plant appears consistently.

An exemplary embodiment of the present application provides a composition for changing the flower color of petunias and a method for changing the flower color of petunias.

In addition, an exemplary embodiment of the present application provides a genome-edited petunia plant having a color variation trait produced by the production method of the present application and seeds in which the genome of the plant is edited.

The petunia plant having a color variation trait according to the present application is a plant in which an F3H gene of a flavonoid biosynthetic route affecting anthocyanin pigments is edited using a CRISPR/Cas9 system, and is a genome-edited plant in which petunia-derived F3H gene is knocked out.

The genome-edited petunia plant according to an exemplary embodiment of the present application has a remarkably reduced anthocyanin content in a petal compared to wild-type petunias, so that it is characterized in that the petals of wild-type petunia have deep violet petals, whereas the genome-edited petunia has pale pink petals.

The present application also provides a genome-editing composition for mutating the flower color of petunia plant, containing, as an effective ingredient, a complex of a guide RNA specific for a target sequence of petunia-derived F3H gene and an endonuclease protein. The genome-editing composition of the present application includes a complex of a guide RNA specific for a target sequence of an F3H gene and an endonuclease protein, so that when petunia plant is treated with the composition, the complex of the guide RNA and the endonuclease protein may act as RNA gene scissors to edit a target gene.

MODES OF THE INVENTION

Materials and Methods
I. RNP-Mediated Transformation
1. Preparation and Extraction of Petunia Protoplasts After culture seedlings of petunia 'midnight' (PanAmerican Seed, USA) obtained by germinating seeds in vitro were grown for 3 weeks, young leaves were taken, pre-treated with 13% mannitol cell protoplast washing (CPW), and then treated by immersion into a VCP enzyme (Viscozyme+Pectinex+Celluclast) and an MC enzyme (Macrozyme+Cellulase), respectively for enzymatic degradation. After shaking culture was performed in the dark state at 40 rpm and 25° C. for 3 hours, centrifugation was performed at 600 rpm for 5 minutes, and purification was further performed through re-suspension and centrifugation in a CPW (w/v) solution including 25% sucrose. Experiments were performed three times biologically and technically to optimize the enzyme treatment and yield for the protoplasts.

2. Determination of Transformation Efficiency Using GFP Fluorescence Gene

Figure 3:
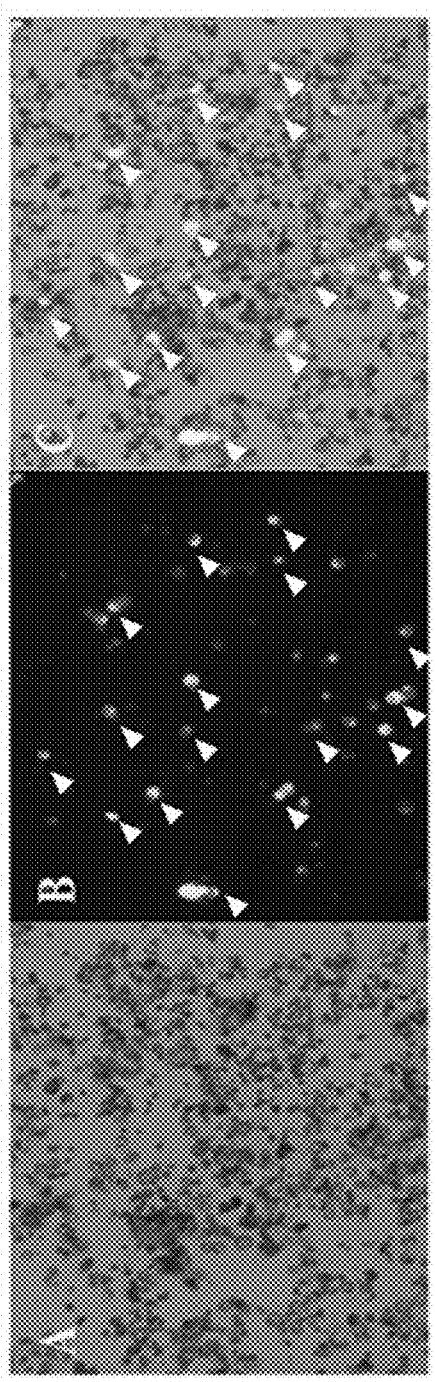
FIG. 3 is a set of fluorescence photographs of *petunia* protoplasts transduced with a vector (PBI221: GFP) including a reporter gene GFP. The triangular parts indicate the parts where GFP is expressed.
Figure 4:
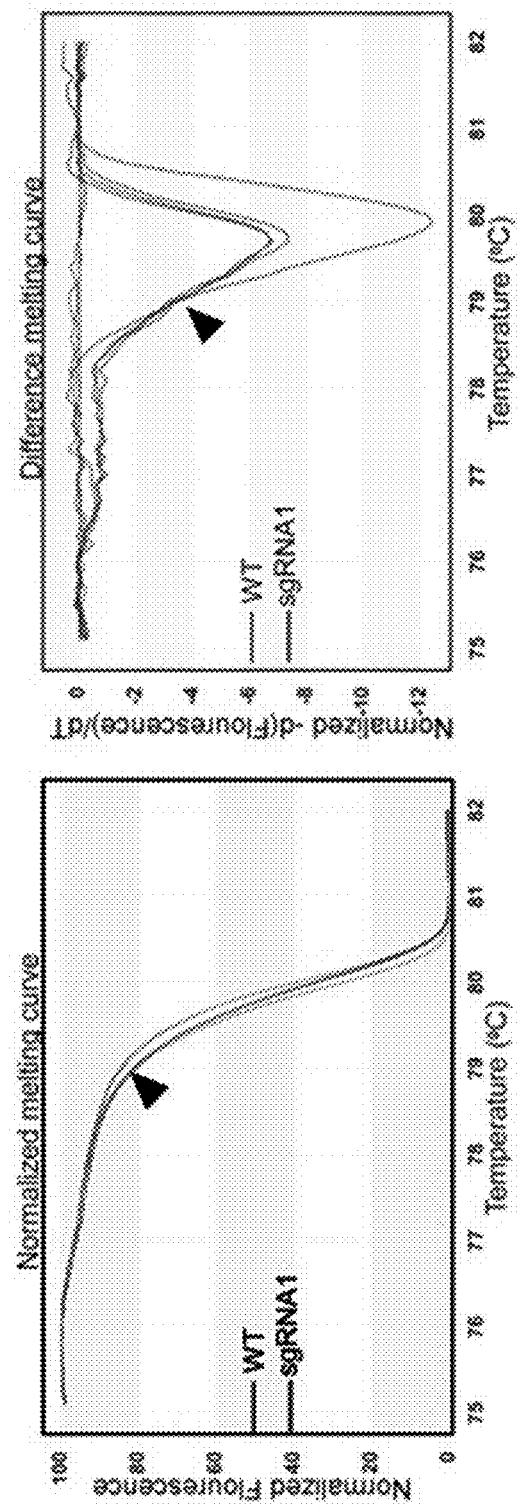
FIGS. 4, 5, 6, 7 and 8 illustrate the results of high resolution melting (HRM) analysis of genomic DNA isolated from wild-type and genome-edited protoplasts.
Figure 5:
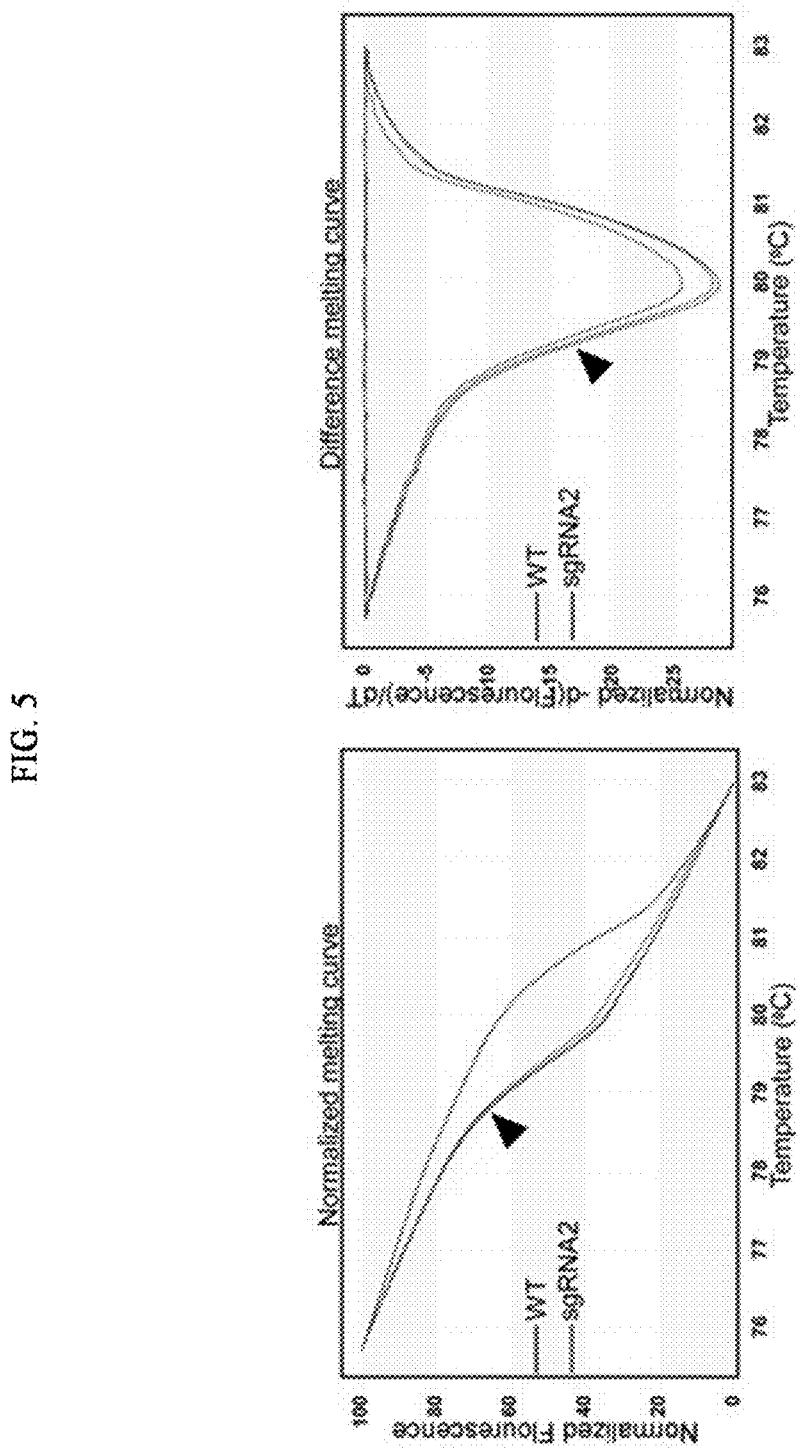

In the present application, in order to increase the transduction rate in the protoplasts of petunia, the protoplasts were treated at different concentrations of polyethylene glycol (PEG) for a culture period to optimize the transduction rate by confirmation through the expression of a green fluorescent protein (GFP). The purified protoplasts were re-suspended in a CPW solution containing a 9% (w/v) mannitol solution, and then stabilized at 4° C. for 1 hour. Thereafter, protoplasts were collected by centrifugation at 600 rpm for 5 minutes, and the cell density was adjusted to $10^6$ cells/ml using 300 µl of a MaMg solution (0.5 mM MES, 0.04 M mannitol, and 15 mM $MgCl_2$). 250 µl of protoplast cells ($2.5\times10^5$ cells/ml) were mixed with 50 µg of a plasmid vector PBI221 including a GFP coding gene (PBI221::GFP). Then, after 270 µl of a PEG solution [40% (w/v) PEG4000 (Sigma-Aldrich), 0.4 M mannitol, and 0.1M $Ca(NO_3)_2$] prepared in advance was added thereto and mixed well, the resulting mixture was incubated at room temperature for 20 minutes. Thereafter, in order to wash the PEG solution, after 250 µl of a washing solution (CPW containing 9% (w/v) mannitol) was added thereto and mixed well, the resulting mixture was reacted at room temperature for 10 minutes. After 500 µl, 1 ml, 2 ml, and 3 ml of the washing solution were sequentially added thereto by the method as described above, the additional washing was performed by incubation at an interval of 10 minutes, and finally, a protoplast pellet obtained by centrifugation at 600 rpm for 5 minutes was transferred to 1 ml of a colony-inducing medium and cultured in the dark at 25° C. A transformation rate was calculated based on the number of cells transformed with GFP under a green fluorescence microscope after 24 hours (FIGS. 1 and 3).

3. Cas9 Protein Recombination, Guide RNA Design, and RNP Transduction

Figure 2:
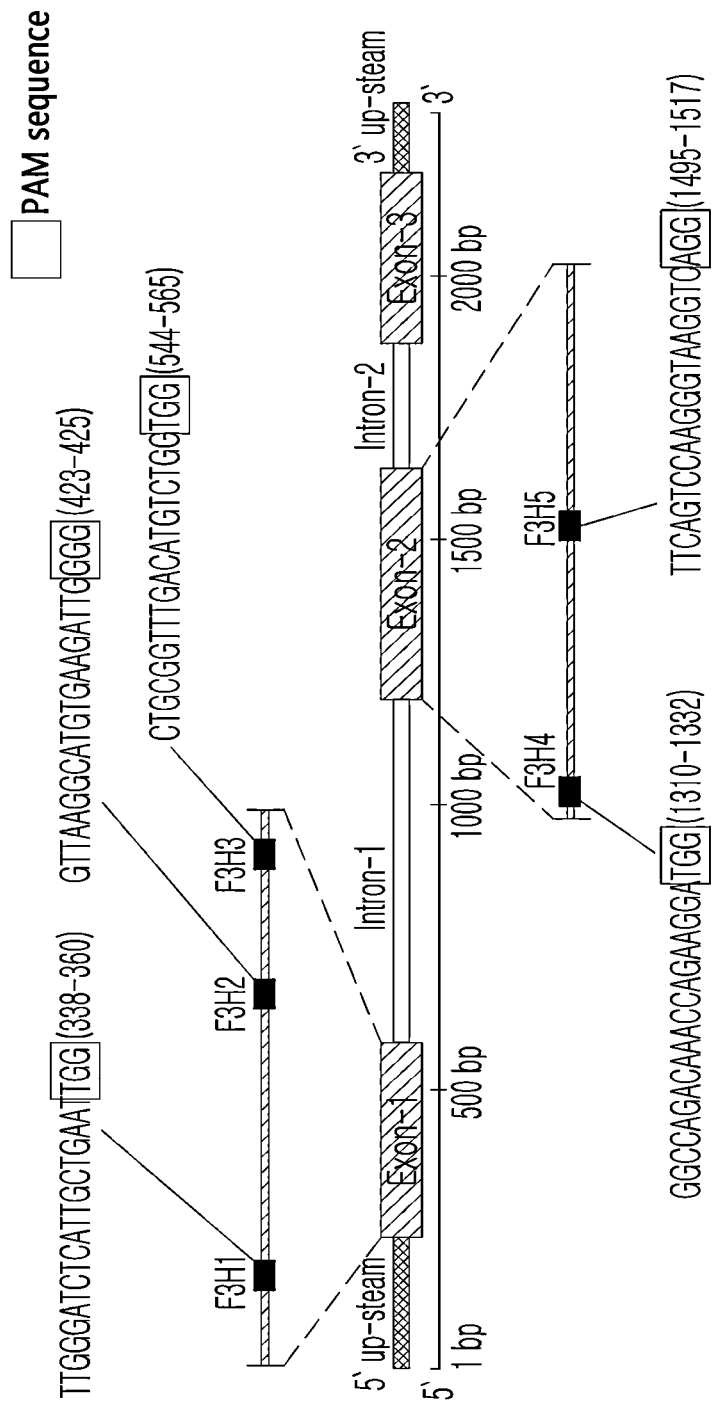
FIG. 2 illustrates five flavanone 3-hydroxylase (F3H) target sgRNA sites determined using CRISPR RGEN tools. The square box parts indicate the 3 bp bases of the PAM motif.

A recombinant Cas9 protein (160 kD) used in the experiment was purchased from ToolGen, Inc. (Korea) and used, and the F3H locus of petunia 'midnight' was amplified and sequenced based on the gene information (GenBank accession no. AF022142.1). Thereafter, the target sites of five other F3H sgRNAs were determined with high out-of-frame scores by targeting the first and second exons of the F3H gene using CRISPR RGEN Tools (http://rgenome.net/) (FIG. 2, Table 1).

Amplification of the intracellular sgRNA target site was performed with the primers disclosed in Table 2. A gene scissors complex using the petunia protoplasts was created at a molecular ratio of Cas9: sgRNA=1.5:3. In order to introduce the prepared complex into protoplast cells, 20 µl of a reaction solution including 2 µl of a Cas9 protein buffer, 27 µg of a Cas9 protein, 80 µg of sgRNA, and deionized water was prepared. This reaction solution was uniformly mixed with the protoplasts suspended in 300 µl of a MaMg solution (0.5 mM MES, 0.4 M mannitol, and 15 mM $MgCl_2$), and then reacted with the prepared PEG solution at room temperature for 20 minutes. The subsequent washing process is the same as for PEG-based GFP plasmid transformation.

4. Detection and Prediction of Mutation Frequency at F3H Locus

Genomic DNA was extracted from the transformed protoplasts using an i-genomic Plant DNA Extraction Mini Kit (Intronbio, Seoul, Korea). A high resolution melt curve analysis was performed to detect the site-directed mutations induced by an RNP at the F3H locus. For this purpose, the target genomic regions of the F3H locus were amplified from the wild type (WT) and the sgRNA transformant using Phusion®High-Fidelity PCR Kit (NEB, USA) and a nested PCR primer (Table 3) according to the manufacturer's protocol. The HRM analysis was performed in an Illumina Eco Real-Time PCR System (Illumina, CA, USA) using 10 µl of a total reaction volume including 2×HRM Master mix supplemented with 2.5 mM $MgCl_2$ and Eva Green dye (PhileKorea, Daejeon, Korea), 100 ng of a template amplified in advance, and 0.2 µM each of forward and reverse primers. PCR amplification was performed by a combination of an initial denaturation step (95° C. for 2 minutes) followed by 40 cycles of 95° C. for 10 seconds, annealing at 60° C. for 30 seconds, and an elongation step. In order to confirm the specificity and dissociation kinetics of the oligonucleotide annealing of PCR products using preset parameters of an Eco Real-Time device, dissociation was performed in a final cycle of 95° C. for 15 seconds, 55° C. for 15 seconds, and 95° C. for 15 seconds under a temperature gradient (55 to 95° C.) condition. Experiments on all used samples were performed in triplicate, and genotypes were designated by comparing lysis curve profiles between WT and sgRNA samples. In order to confirm and evaluate the mutation frequency of InDel (Insertion/Deletion) generated by RGENs in the transformed protoplasts, the F3H gene target site was amplified with nested PCR primers (Table 2), and the sequence was determined according to the Illumina MiSeq platform. As a result, InDel mutations around the RGEN cleavage site were observed, and the mutation frequency was calculated with each F3H-RGEN transductant.

TABLE 1

| Target | sgRNA | Sequence (5'-3') (SEQ. ID NO.) | Strand Direction | Position (bp) |
|---|---|---|---|---|
| F3H1 | F3H1-RGEN | TTGGGATCTCATT GCTGAATTGG (1) | - | 158-180 |
| F3H2 | F3H2-RGEN | GTTAAGGCATGTG AAGATTGGGG (2) | + | 428-450 |
| F3H3 | F3H3-RGEN | CTGCGGTTTGACA TGTCTGGTGG (3) | + | 586-608 |
| F3H4 | F3H4-RGEN | GGCCAGACAAACC AGAAGGATGG (4) | + | 765-787 |
| F3H5 | F3H5-RGEN | TTCAGTCCAAGGG TAAGGTCAGG (5) | - | 1431-1453 |

TABLE 2

| | 1st PCR | | | 2nd PCR | | | |
|---|---|---|---|---|---|---|---|
| Target site | Primer Sequence (5'-3') (SEQ ID NO) | Annealing Regions (pp) | Primer Sequence for Deep target sequencing (5'-3') (SEQ ID NO) | Primer Sequence for HRM (5'-3') (SEQ ID NO) | Annealing Regions (bp) | Product Size (bp) |
| F3H1 | F1: GGCACCTTCAACAT TAACAGC (6) R1: AACGCCCCAATCTT CACATG (7) | 329-449 | 2F1: ACACTCTTTCCCTACACGACGCTCTTCC GATCTgcaccttcaacattaacagcatt (8) 2R1: GTGACTGGAGTTCAGACGTGTGCTCTT CCGATCTccccaatcttcacatgcctt (9) | GCACCTTCAACATTA ACAGCATT (10) CCCCAATCTTCACAT GCCTT (11) | 246-445 | 199 |

TABLE 2-continued

| Target site | 1st PCR Primer Sequence (5'-3') (SEQ ID NO) | Annealing Regions (pp) | 2nd PCR Primer Sequence for Deep target sequencing (5'-3') (SEQ ID NO) | Primer Sequence for HRM (5'-3') (SEQ ID NO) | Annealing Regions (bp) | Product Size (bp) |
|---|---|---|---|---|---|---|
| F3H2 | F2: GCTTACAACCAATTC AGCAATG (12)<br>R2: GTCTGGTGGCAAGA AAGGTG (13) | 329-576 | 2F2: ACACTCTTTCCCTACACGACGCTCTTCC GATCTccaattcagcaatgagatccca (14)<br>2R2: GTGACTGGAGTTCAGACGTGTGCTCTT CCGATCTacatgtcaaaccgcagcttt (15) | CCAATTCAGCAATGA GATCCCA (16)<br>ACATGTCAAACCGCA GCTTT (17) | 338-559 | 221 |
| F3H3 | F3: AAGGCATGTGAAGA TTGGGG (18)<br>R3: GTCACTTCACATTT GTCTTCCG (12) | 426-689 | 2F3: ACACTCTTTCCCTACACGACGCTCTTCC GATCTgttgtggatcatgggttga (20)<br>2R3: GTGACTGGAGTTCAGACGTGTGCTCTTC CGATCTgcatgttgaatactacttggtcg (21) | GTTGTGGATCATGGG GTTGA (22)<br>GCATGTTGAATACTA CTTGGTCG (23) | 456-639 | 183 |
| F3H4 | F4: GGAACGGTAATGGA AGAGCA (24)<br>R4: CATGACGGATAGCC AGGAA (25) | 1159-1727 | 2F4: ACACTCTTTCCCTACACGACGCTCTTCC GATCTtgtgacctactttcgtaccca (26)<br>2R4: GTGACTGGAGTTCAGACGTGTGCTCTT CCGATCTtacccaaagtgtcctgagcc (27) | TGTGACCTACTTTTC GTACCCA (28)<br>TACCCAAAGTGTCCT GAGCC (29) | 1236-1496 | 260 |
| F3H5 | F5: AGGGTGAAGTGGTC CAAGA (30)<br>R5: TTGAACCGTCCATTG CTCA (31) | 1231-1924 | 2F5: ACACTCTTTCCCTACACGACGCTCTTCC GATCTggcatgtgtggatatggacc (32)<br>2R5: GTGACTGGAGTTCAGACGTGTGCTCTT CCGATCTggctgaacagtgatccaagt (33) | GGCATGTGTGGATAT GGACC (34)<br>GGCTCGAACAGTGATC CAAGT (35) | 1437-1619 | 182 |

Example 1. Improved Transient Expression System in Petunia

The protoplast isolation and transient expression system of petunia has not been sufficiently investigated by previous studies and some of the available methods have not been improved for 30 years. The yield, viability, and efficient transduction should be first preceded by successful protoplast isolation. Protoplast isolation is affected by various factors such as the type of explant, enzyme concentration, culture time and buffer composition. In the present application, a method for isolating petunia protoplasts and a transient expression system have been added and improved. In an enzyme combination (MC) in which a 1.5% cell enzyme almost similar to a previous petunia protoplast-based experiment (Subburaj et al. 2016 Plant Cell Rep. 35:1535) and 0.25% Macerozyme were used, the maximum protoplast yield of a fresh weight of $1.52\pm0.23\times10^6$ cells/g was observed. However, when a modified enzyme combination (VCP) including 0.6% Celluclast, 0.6% Pectinex, and 1.2% Viscozyme was used, a high protoplast isolation yield of up to $6.90\pm0.18\times10^6$ cells was confirmed by culture for 3 hours. Further, for the protoplasts obtained by VCP, the viability of the protoplasts amounted to 94% in a test with fluorescein diacetate (FDA), which is a fluorescent dye, confirming that it was higher than that of the MC enzyme combination (Table 3). Through this, the results of the present application are believed to significantly improve the isolation and yield of undamaged and living protoplasts in petunia transient gene expression studies.

TABLE 3

| Enzyme components | YAKULT(powder)-MC enzyme | | Novozymes (liquid)-VCP enzyme | | | Yield of protoplast (*$10^6$ cells/g FW) | Viability Test by FDA Alive cells (%) |
|---|---|---|---|---|---|---|---|
| | Cellulase R-10 (%) | Macerozyme R-10 (%) | Celluclast (%) | PetinEX (%) | Viscozyme (%) | | |
| EC1 | 1.5 | 0.25 | — | — | — | 1.82 ± 0.23 | 89.04± |
| EC2 | 1.5 | 0.5 | — | — | — | 3.20 ± 0.31 | 85.06± |
| EC3 | 1.5 | 0.8 | — | — | — | 2.37 ± 0.33 | 86.53± |
| EC4 | — | — | 0.2 | 0.2 | 0.4 | 3.79 ± 0.10 | 91.32± |
| EC5 | — | — | 0.4 | 0.4 | 0.8 | 5.79 ± 0.19 | 93.10± |
| EC6 | — | — | 0.6 | 0.6 | 1.2 | 6.90 ± 0.18 | 94.30± |
| EC7 | — | — | 0.8 | 0.8 | 1.6 | 4.97 ± 0.19 | 93.46± |

The petunia protoplasts ($2.5\times10^5$ cells) extracted for the confirmation of transduction were transduced with 50 μg of a vector (PBI221) including a reporter gene GFP using 40% PEG4000. As illustrated in FIG. 3, GFP expression was confirmed after 24 hours and an expression of 50% was shown in previous studies, whereas a higher expression of 55% was confirmed in the present application. In the present application, PEG4000 was used as compared to the previous studies, and it is believed that the culture time was shortened to 20 minutes to enhance the viability and vitality of the petunia protoplasts with high reproducibility. As a result of this study, it is believed that the improved transient expression system will be useful for studies of petunias and other eggplant family plants and for studies of target gene mutations in the future.

Example 2. Direct Delivery of RGEN RNP for Target Mutagenesis of F3H Gene in Petunia Protoplast Studies In order to cause target site mutations in petunia F3H, sgRNAs (F3H1, F3H2, F3H3, F3H4 and F3H5) were designed for a target site corresponding to the F3H locus (FIG. 2). The designed sgRNA has 23 nucleotides (including 3 bp PAM), and is paired with the corresponding 20 nucleotides at the target site of the F3H locus to help CRSPR/Cas9 make a site-specific double strand break (DSB).

Compared to other genome editing tools (ZFN or TALENS), the CRISPR/Cas9 system has been considered to be more effective in preparation, transmission, and production for causing target-specific mutations. Direct transmission of DNA-free proteins such as the RNP complex (Cas9-sgRNA) to living cells is not restricted by GMO regulations, and reduces off-target effects. Therefore, in the present application, a direct introduction of an RNP complex (purified Cas9 protein+sgRNA synthesized in vitro) was attempted in petunia protoplasts in order to mutate endogenous F3H genes, as described in a previous study (Subburaj et al., 2016 Plant Cell Rep. 35:1535) (FIG. 1).

A high resolution melting (HRM) curve analysis was used to determine if there was an Indel mutation in F3H among the CRISPR/Cas9-induced mutations in the protoplasts. For this purpose, the HRM curves of DNA samples of a control to which an RNP was not introduced and the protoplasts transformed with an RNP were compared. In the protoplasts, the RGEN target site of the F3H locus was amplified using site specific nested PCR primers. As can be seen in FIGS. 4 to 8, the HRM analysis can clarify the distinction between WT and sgRNA mutants (indicated by triangles) at all five target sites of F3H according to the pattern of the differential curve, so that the CRISPR/Cas9-induced mutation in the protoplast cells could be confirmed in a simple and efficient manner (FIGS. 4 to 8).

Example 3. Confirmation of RGEN RNP-Inducible Transformed Cells and Mutation Morphology in Petunia F3H Gene by Targeted Deep Sequencing Targeted deep sequencing was performed to confirm the transformed cells and mutation morphology of the target gene F3H in the RNP-introduced protoplasts. DNA was extracted from the protoplast cells transformed with a combination of RNPs using 5 sgRNAs of F3H1 to F3H5, and then first amplified using the primers disclosed in Table 2. It could be confirmed that mutations did not occur in the control (WT) and protoplast cells transformed only with a Cas9 protein, whereas mutation forms such as insertions and deletions occurred at five RNP binding sites constructed to target the F3H gene. Depending on the constructed guide RNA binding site, a mutation rate of 0.8 to 49.3% occurred, and an average mutation rate of about 20.8% at the F3H locus was induced (Table 4).

In Table 4, a means the number of inserted sequences in the mutation rate, b means the number of deleted sequences, and c means a mean and standard deviation error value calculated only for F3H1 to F3H5.

TABLE 4

| Targeting sites | Wild-type transfectants | | | Cas9 protein transfectants | | | F3H-RGEN transfectants | | | | |
|---|---|---|---|---|---|---|---|---|---|---|---|
| | Total | Indel | Indel frequency (%) | Total | Indel | Indel frequency (%) | Total | Ins[a] | Del[b] | Indel | Indel frequency (%) |
| sgRNA1 | 72252 | 0 | 0 | 71050 | 0 | 0 | 73394 | 433 | 190 | 623 | 0.8 |
| sgRNA2 | 67665 | 3 | 0 | 68794 | 5 | 0.007 | 47137 | 11703 | 11517 | 23220 | 49.3 |
| sgRNA3 | 65532 | 6 | 0 | 64641 | 8 | 0.012 | 69584 | 11824 | 2447 | 14271 | 20.5 |
| sgRNA4 | 53956 | 3 | 0 | 53616 | 4 | 0.007 | 49324 | 5364 | 5228 | 10592 | 21.5 |
| sgRNA5 | 58863 | 7 | 0 | 56021 | 18 | 0.032 | 65196 | 1507 | 6184 | 7691 | 11.8 |
| Average[c] | — | — | 0 ± 0 | — | — | 0.012 ± 0.004 | — | 6166.2 ± 2171.5 | 5113.2 ± 1714.8 | — | 20.8 ± 7 |

[a]Numbers of insertions were analyzed in the case of F3H.RGEN transformants.
[b]Numbers of deletions were analyzed in the case of F3H.RGEN transformants.
[c]Values of average and standard deviation error calculated only for F3H1, F3H2, F3H3, F3H4, and F3H5.

When compared to an example in which the present applicant attempted editing by applying CRISPR/Cas9 to an existing nitrate reductase (NR) gene as a target using the same petunia variety and protoplast (Subburaj et al., 2016), this can be a technical development which brings about a high mutation efficiency in terms of an average mutagenesis rate (NR 14.9% vs. F3H 20.8%) and a maximum mutation rate (NR 34.7% vs. F3H 49.3%).

Figure 9:
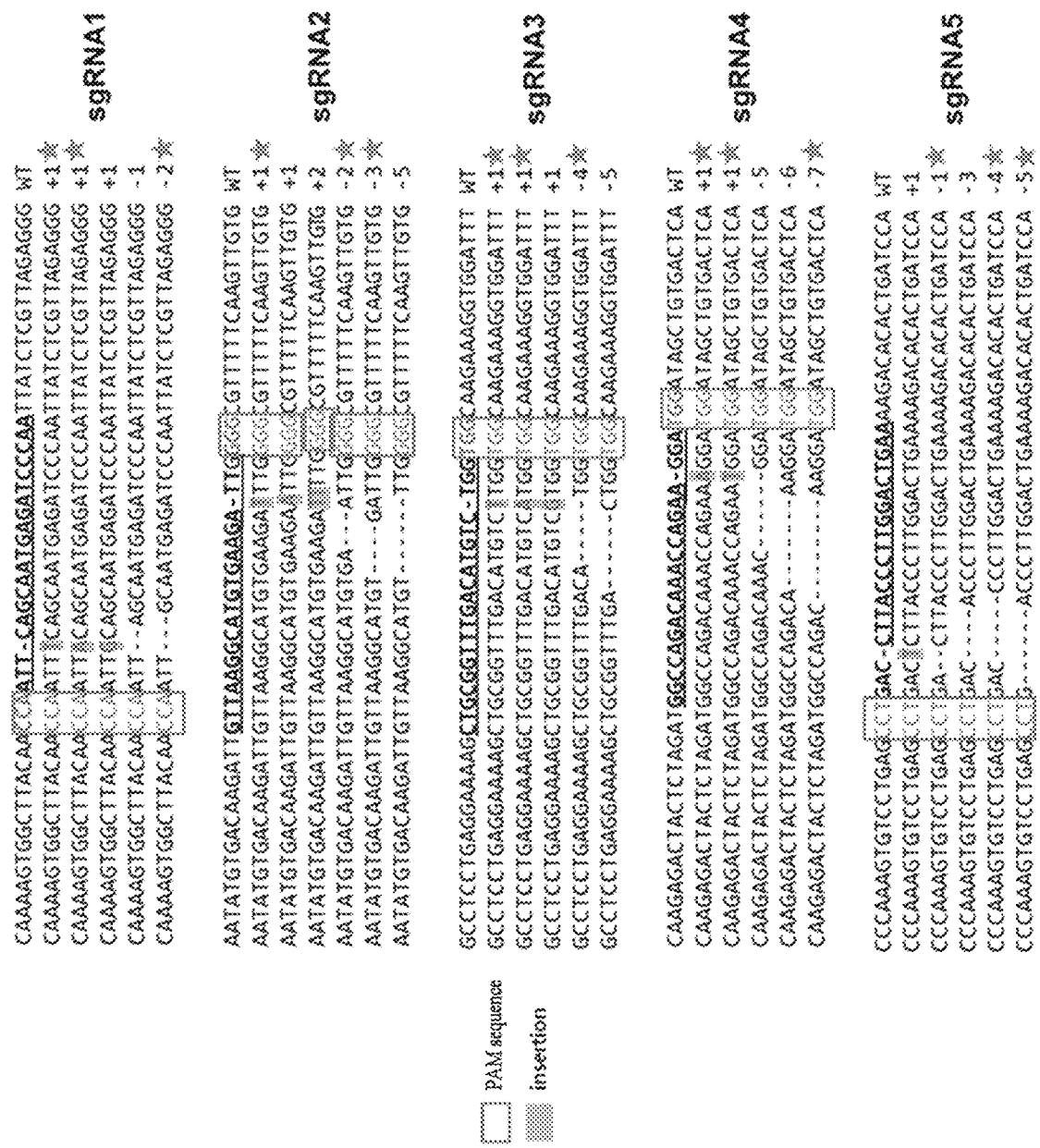
FIG. 9 is representative base mutation information of the F3H locus by targeted deep sequencing of cells in which genome editing is induced using sgRNA1 to 5. The underlined and bold letters indicate the target sequence of nucleases, and the square box parts indicate the 3 bp bases of the PAM motif, and the shaded part means the insertion mutation. The asterisk (*) next to the mutant sequence shows the type of mutant form with high frequency according to sgRNA.

For the mutation morphologies generated at the F3H locus, as a result of investigation by averaging the constructed five RNPs, it could be seen that the ratio of deletion and insertion mutants was 45.4:54.6, and the mutation in a form in which a new base was inserted to the target site was shown to be slightly higher. Although there were differences depending on the constructed RNP, it could be seen that cells induced with a base deletion size of 1 to 7 bp and a base insertion size of 2 bp were generated (FIG. 9).

Figure 6:
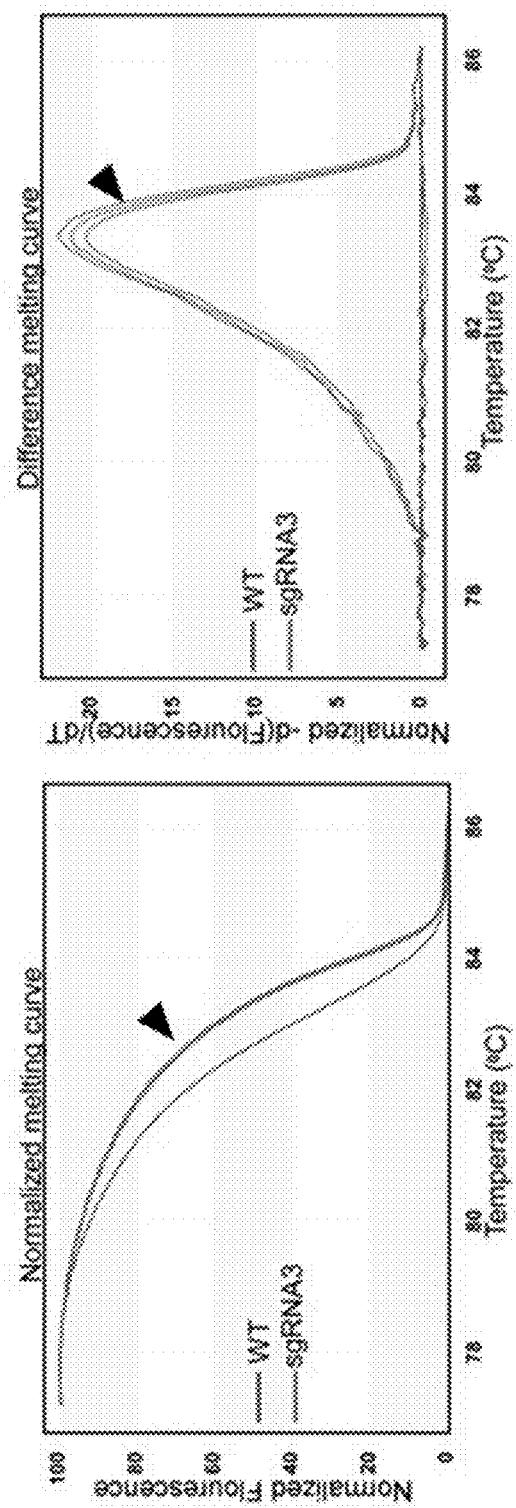
Figure 7:
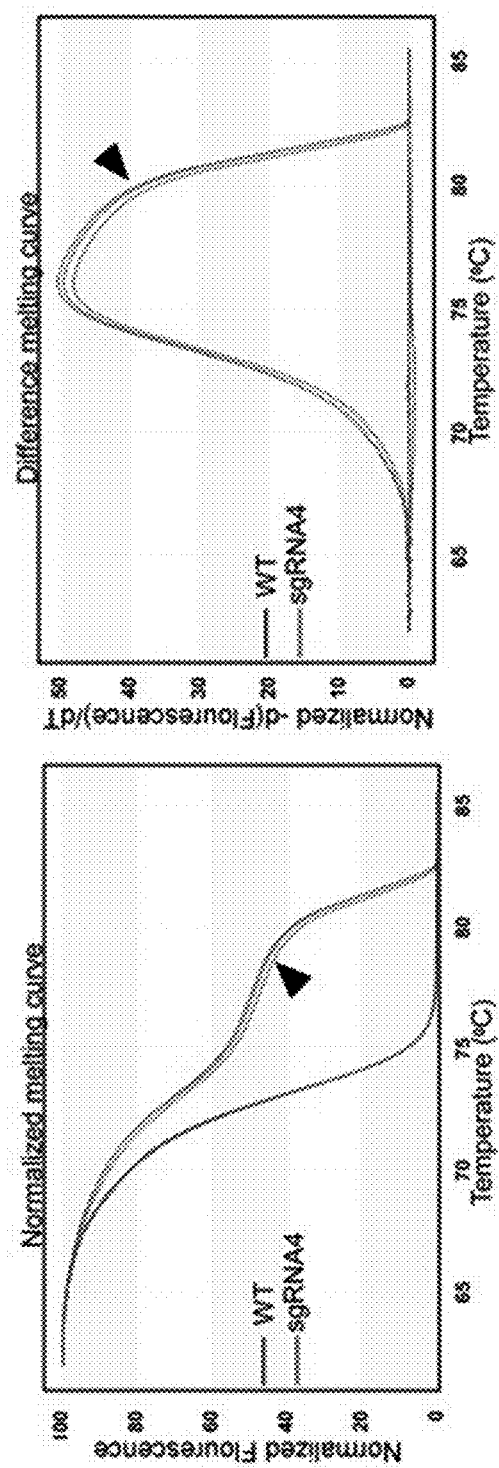
Figure 8:
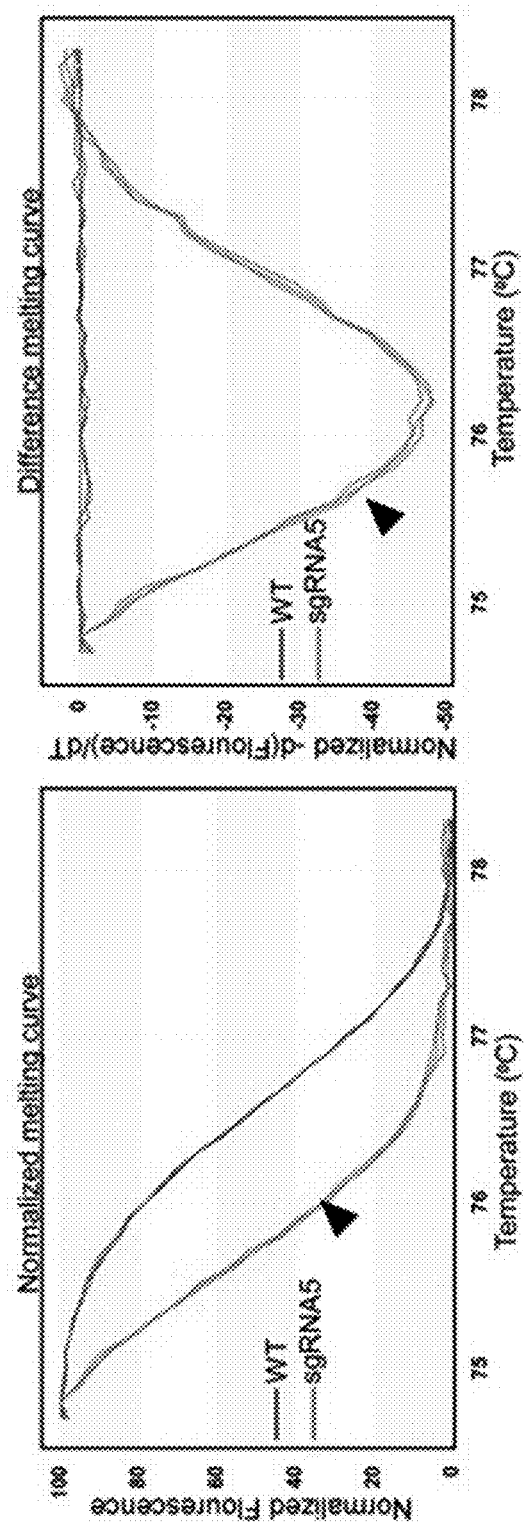
Figure 10:
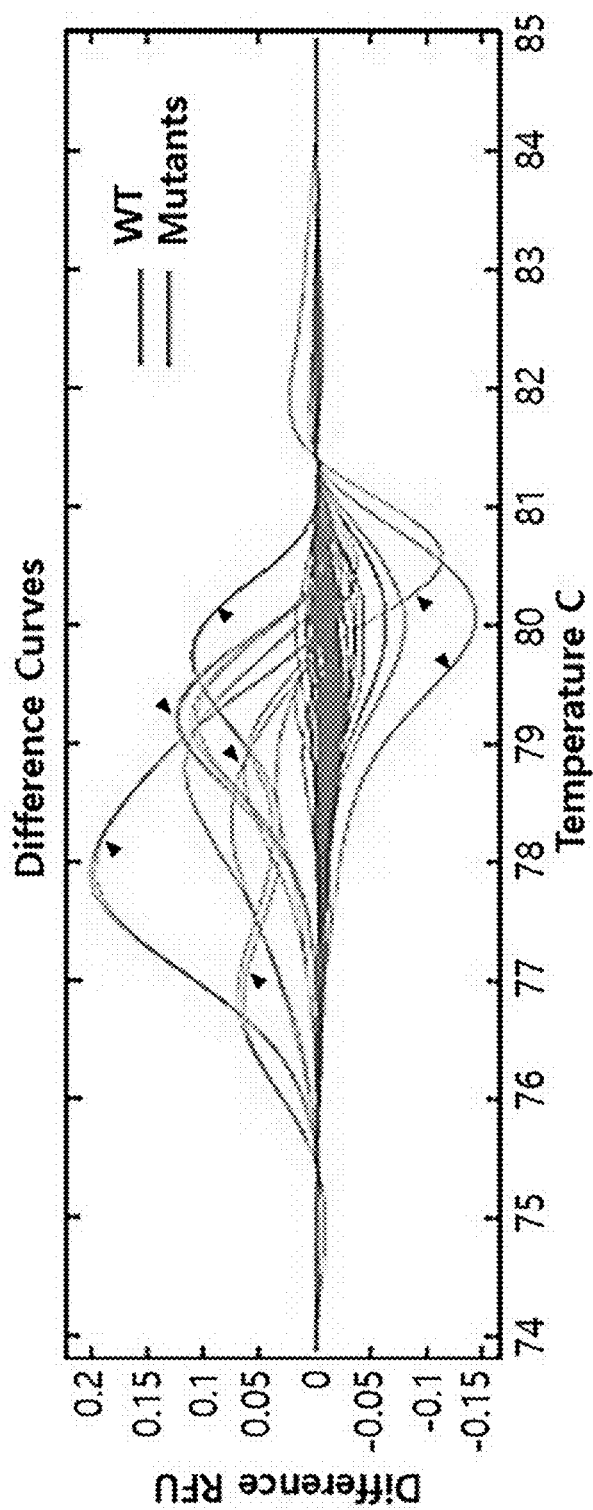
FIG. 10 illustrates the results of high resolution melting (HRM) analysis for confirming mutations in RNP-mediated transformed regenerated T0 *petunia*.
Figure 11:
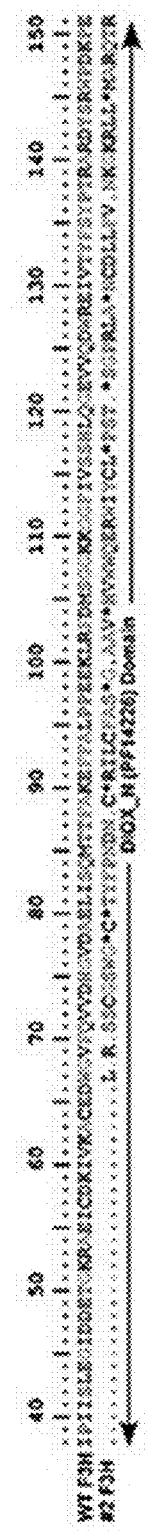
FIG. 11 illustrates the amino acid analysis results of wild-type F3H (named WTF3H) and mutant F3H (named #2F3H) in *petunia*.

Example 4. CRISPR/Cas9-Mediated Mutation and Genotype Analysis in Regenerated T0 Petunia Plant After the cell colony of the protoplasts transduced with an RNP was cultured in a callus-inducing medium, a green callus began to appear about two weeks later. A callus islet was incised and subcultured to induce the formation of shoots. Seedlings grown from the same callus islet were considered to be independent T0 plants. 39, 48, 62, 57, and 35 T0 plants were obtained from F3HRGEN using 5 F3H1 to F3H5 sgRNAs, respectively. In order to confirm the mutations induced by CRISPR/Cas9, DNA samples were prepared from each plant and HRM analysis was performed at the target site (FIG. 10). The results are illustrated in FIG. 6, and the curve represented by triangles refers to a mutant. It could be seen that mutations were induced by showing a distinct HRM curve in 8 plant DNA samples among 48 plants at the target position of F3H2, but no particular HRM curve distinguishable from the wild type was confirmed at the target positions of F3H1 and F3H3 to F3H5. In order to accurately verify the mutations, the F3H2 target positions of the eight plants showing the distinct HRM curves were amplified and analyzed by direct Sanger sequencing. As a result of a DNA chromatogram, a mutant F3H allele (allele #2) in which a T base was inserted at the position 200 in the coding sequence (CDS) of wild-type F3H (allele #1) in one plant among the eight plants was confirmed. The mutant F3H allele #2 caused a frameshift to cause an in-frame premature termination codon at amino acid 78, and a large amount of truncated proteins was produced during mRNA translation, so that it was predicted that the destruction of activity of the non-haemdioxygenase (DIOX_N) in morphine synthesis N-terminal would ultimately result in the total or partial loss of F3H functionality (FIG. 11).

In addition, the sequencing analysis results and indel results of F3Ha and F3Hb, which are gene sequences having an SNP in petunia, having undergone RNP-mediated transformation are illustrated in FIGS. 14 to 19 (each target gene is named 1226 P1C7, 1226 P3C5, and 1226 P4C4). It could be seen that a T base insertion mutation was confirmed even in F3Ha or F3Hb having an SNP, and it was confirmed that the indel frequency was 95% or more in the mutants F3Ha and F3Hb in FIGS. 14 to 19, compared to the wild types F3Ha and F3Hb in FIGS. 12 and 13.

Figure 20:
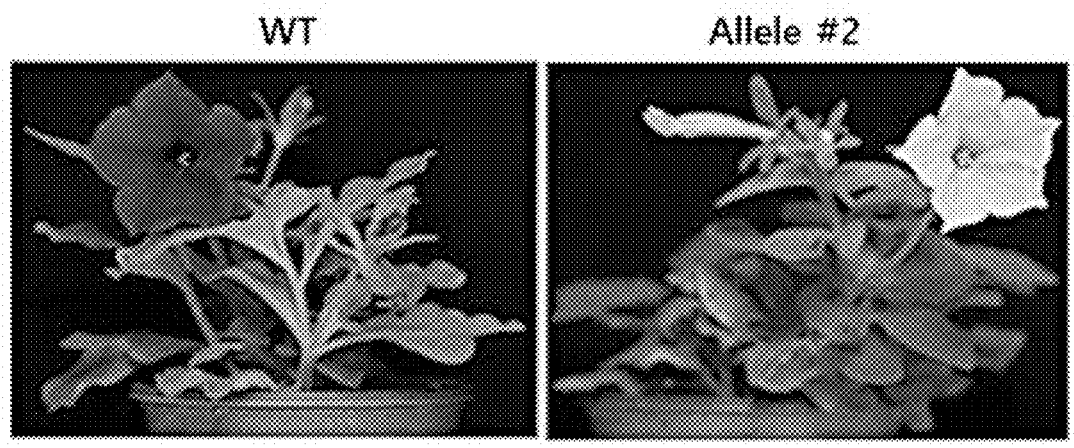
FIG. 20 is a view illustrating the flower colors of *petunia* plants in which wild-type F3H (named WT) and mutant F3H (named Allele #2) have undergone RNP-mediated transformation.
Figure 21:
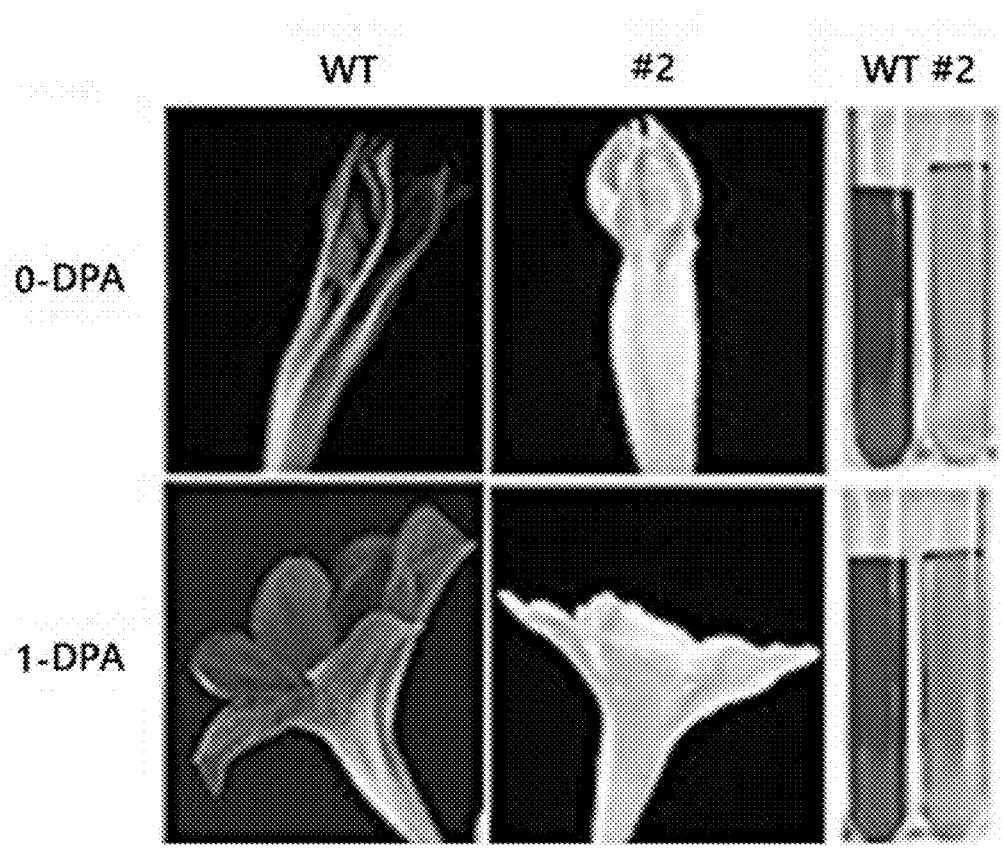
FIG. 21 illustrates the results of planting *petunia* plants in which wild-type F3H (named WT) and mutant F3H (named Allele #2) have undergone RNP-mediated transformation in soil in order to visually evaluate 0-DPA and 1-DPA flower colors.
Figure 22:
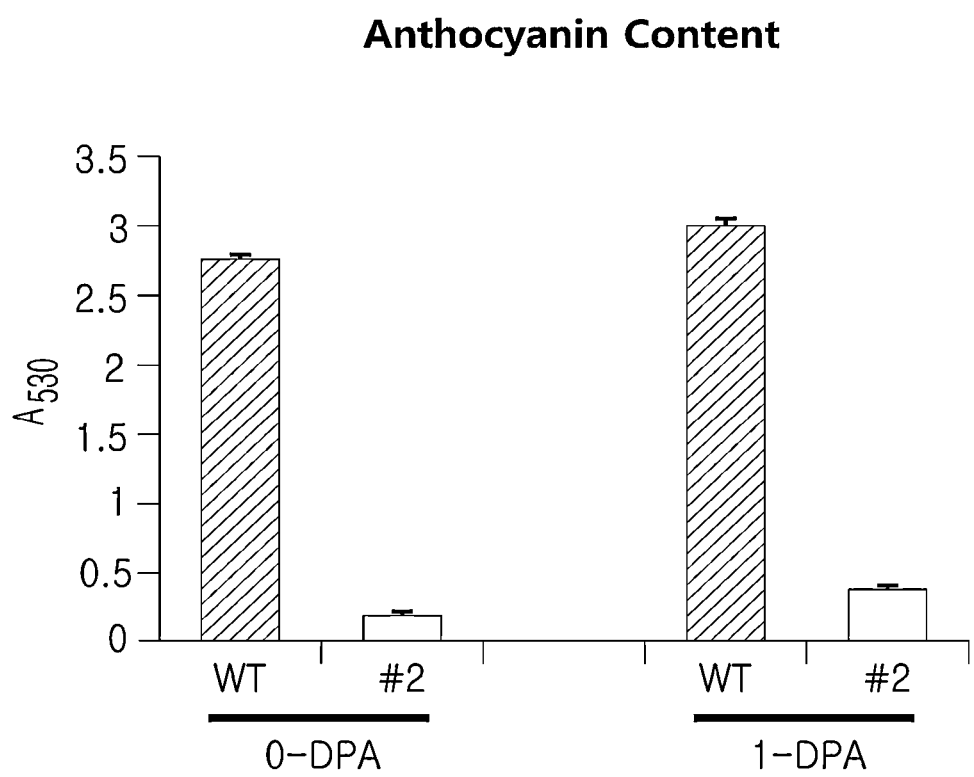
FIG. 22 illustrate the results of measuring the absorbances of anthocyanin contents of 0-DPA and 1-DPA petals of *petunia* plants in which wild-type F3H (named WT) and mutant F3H (named Allele #2) have undergone RNP-mediated transformation.

Regenerated plants were planted in soil for visual evaluation of the flower color phenotype. Flowering began about 4 weeks later, and wild-type petunias had a violet-blue flower color, whereas a plant having mutant F3H allele #2 showed a distinctly modified flower color (FIGS. 20 and 21). The results suggested that a single gene copy of F3H could be mutated by CRISPR/Cas9. The present applicants measured the relative anthocyanin contents in 0 and 1 DPA petals of the wild type and a plant having mutant F3H allele #2 (FIG. 22). As can be seen in FIG. 22, it could be seen that the absorbance value of the petal extract of the plant having mutant F3H allele #2 showed a value remarkably lower than that of the petal extract of the wild-type plant, and the knockout of F3H caused a change in petal color by suppressing the production of anthocyanin. Deep target sequencing was performed to confirm genotype and mutation rate at the target sites of F3H2 in a TO plant. Among the tested eight plants, a single mutation (2.1%) was found, which was putative homozygous with a 1 bp base inserted in the F3H2 target site at the F3H locus, and no particular InDel mutation rate was confirmed compared to the wild type in the remaining plants.

II. Agrobacterium-Mediated Transformation

Petunia (Petunia×hybrida), derived from a hybrid of *P. axillaris* and *P. integrifolia*, has a single copy of F3H (AF022142, Houwelingen et al. 1997).

Recently, the present applicants found an extra copy of the F3H homologous gene due to deletion of SNPs and coding sequences in *P. hybrida* Cv "midnight" (NCBI; AF022142).

In the present example, these genes were named F3Ha and F3Hb and used in this experiment.

1. Preparation of Petunia

Figure 23:
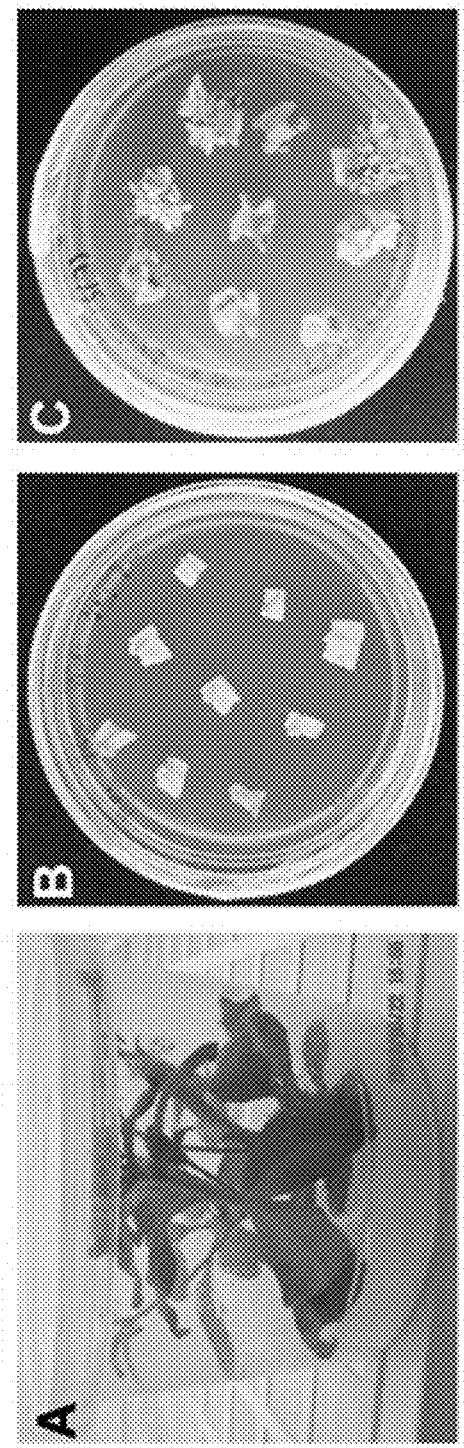
FIG. 23 is a set of views illustrating three-week-old young leaves of *P. hybrida* Cv midnight (A), a state where the leaves are cut into small pieces of about 0.5×0.5 cm for agrobacterium-mediated CRISRP/Cas9 transformation (B), and a state where the leaves are explanted (C).

Experiments were performed by using and culturing young leaves (A of FIG. 23) of 3-week-old *P. hybrida* cv. 'midnight' (PanAmerican Seed, IL).

Figure 24:
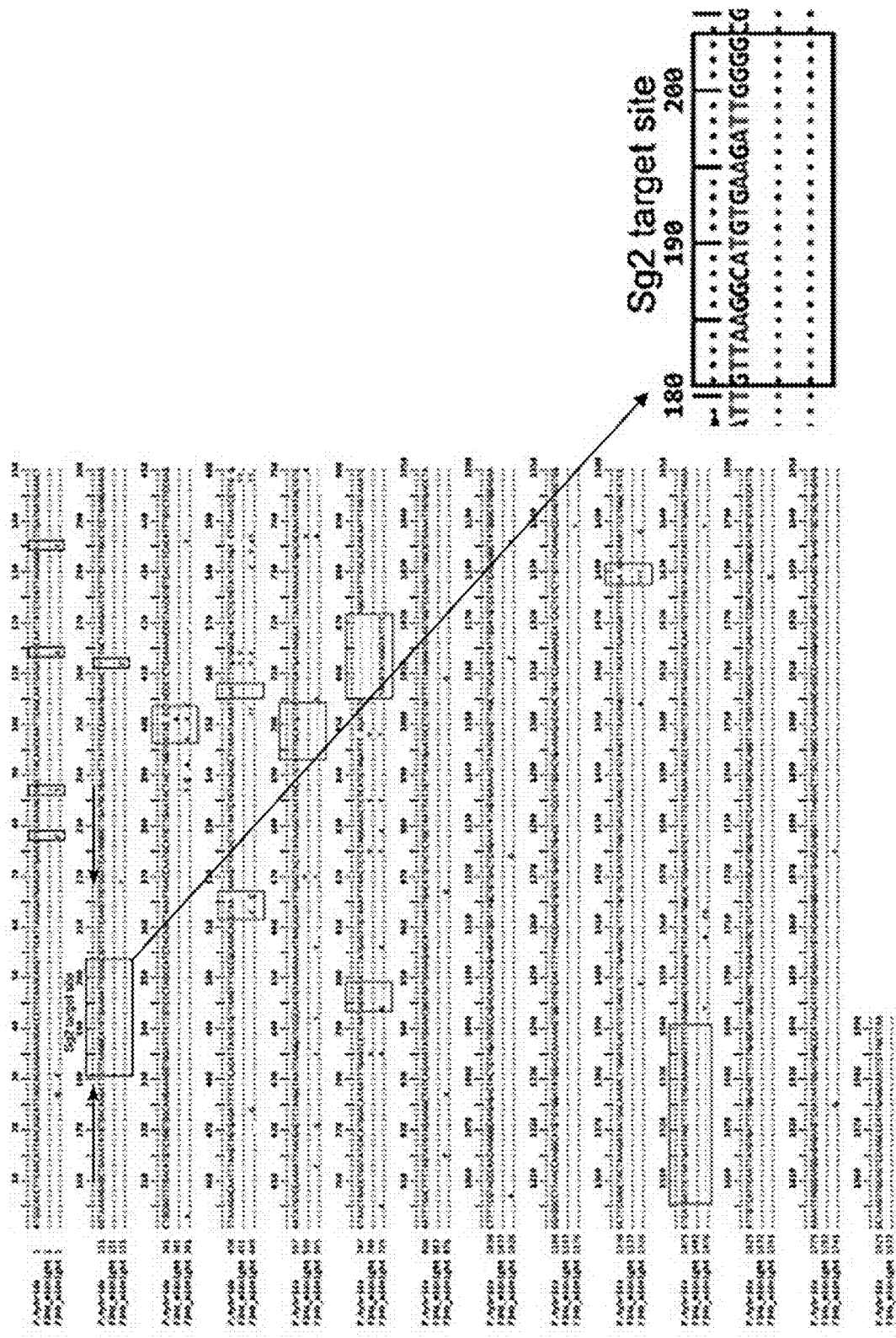
FIG. 24 is a view illustrating the sgRNA target sites (named sg2 target site) of F3Ha and F3Hb determined using CRISPR RGEN tools.

2. sgRNA Design and Vector Construction gRNA was designed for a single target specific site where the first (FIG. 24) exons of the F3Ha and F3Hb genes are conserved through the CRISPR RGEN Tools website (http://rgenome.net/) (Bae et al. 2014). Also, a high-throughput binary vector pBATC (Kim et al., 2016) was obtained from Toolgen Inc. An sgRNA oligo synthesized to construct pBAtc::PhF3H-sgRNA was annealed and inserted into the AarI site of the pBAtC vector.

3. Transformation and Culture

The protocol for Agrobacterium-mediated transformation was performed with reference to the method of Kim et al. 2016. Briefly, petunia was cut into small pieces of about 0.5×0.5 cm (B of FIG. 23), transformed by a co-culture method with Agrobacterium, and then used.

The cut section (explant) obtained from an explant was selectively cultured with basta before transformation. After *Agrobacterium tumefaciens* was streaked on a solid YEP medium [75 mg/L Spectinomycin, 25 mg/L rifampicin, 10 g/L peptone, 5 g/L NaCl, 5 g/L yeast extract, and 1.5% (w/v) agar (pH 7.0)], a single colony produced by culturing *Agrobacterium tumefaciens* at 28° C. was put into 10 ml of a liquid YEP medium containing the same antibiotics, and stirred at 220 rpm at 28° C. until the OD650 reached 0.6 to 0.8.

10 mL of 30% glycerol stock was added to the fully-grown culture bacteria and mixed, and 1 mL each was aliquoted into a 1.5 mL tube, rapidly cooled with liquid nitrogen, and stored at −70° C. 1 mL of the *Agrobacterium tumefaciens* stock stored at −70° C. was put into 200 mL of a liquid YEP medium containing antibiotics one day before inoculation, and shaken at 250 rpm in an incubator at 25° C. until the OD650 reached 0.6 to 0.8. On the day of inoculation, 200 mL of the liquid YEP medium was divided into 50 mL each and centrifuged at 20° C. at 3,270 g for 10 minutes. *Agrobacterium tumefaciens* pellets present in each tube were prepared by adding 15 ml of a liquid co-cultivation medium (CCM; 0.32 g/L B5 salt, 1.67 mg/L BA, 20 mM MES, 0.25 mg/L GA3, 0.2 mM acetosyringone, 3.3 mM L-cysteine, 1.0 mM sodium thiosulfate, 1.0 mM DTT, 3% sucrose, and pH 5.4). Approximately 50 sections were put into a 15 mL co-culture/*Agrobacterium tumefaciens*, sonicated for 20 seconds, and then inoculated for 30 minutes. After each section was removed from the tube and placed on a sterile filter paper to remove moisture, a solid CCM (same as liquid CCM, agar (0.7%)) was also covered with a sheet of filter paper and 10 individuals were placed on that.

Thereafter, the transformed regenerated plants were transplanted into a growth chamber having a photo period of 16 hours (25±1° C.)/8 hours (20±1° C.) and phenotypic analysis was performed (FIG. 23C).

4. Confirmation of Genotype and Mutation Detection

The genomic DNA of the transformed plant was extracted with an i-genomic plant DNA extraction kit (Intronbio, Seoul, Korea). F3H target sites with indel mutations were detected by PCR amplification using primers (SEQ ID NOs: 53 to 59) and target deep sequencing using the Illumina MiSeq platform.

Target deep DNA sequencing of FT2 target sites in the F3Ha and F3Hb loci was performed in TO independently regenerated plants. The results are shown in [Table 5]. In this case, it was marked as a wild type (named plant 1) and a mutant type (named plant 2). It was confirmed that indels were formed in 99% or more of both alleles (Table 5).

Further, it was confirmed that the transformed mutation was a positive mutation in which both alleles were mutated to homozygous at both the F3Ha and F3Hb loci.

Figure 25:
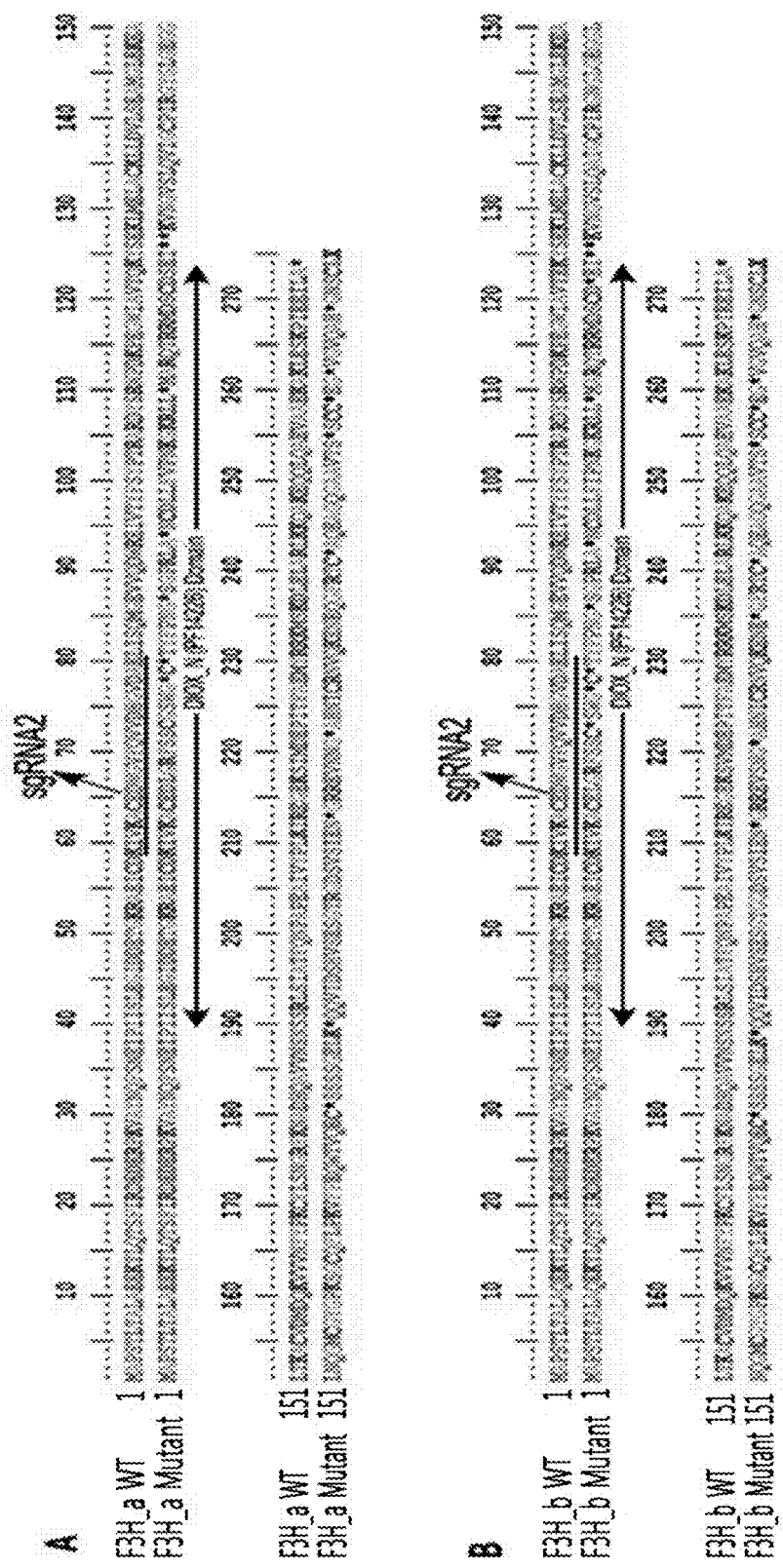
FIG. 25 illustrates the amino acid analysis results of the wild-type F3Ha and F3Hb (F3H_aWT, F3H_bWT) and mutant-type F3Ha and F3Hb (F3H_aMutant, F3H_bMutant) in *P. hybrida* Cv midnight.
Figure 29:
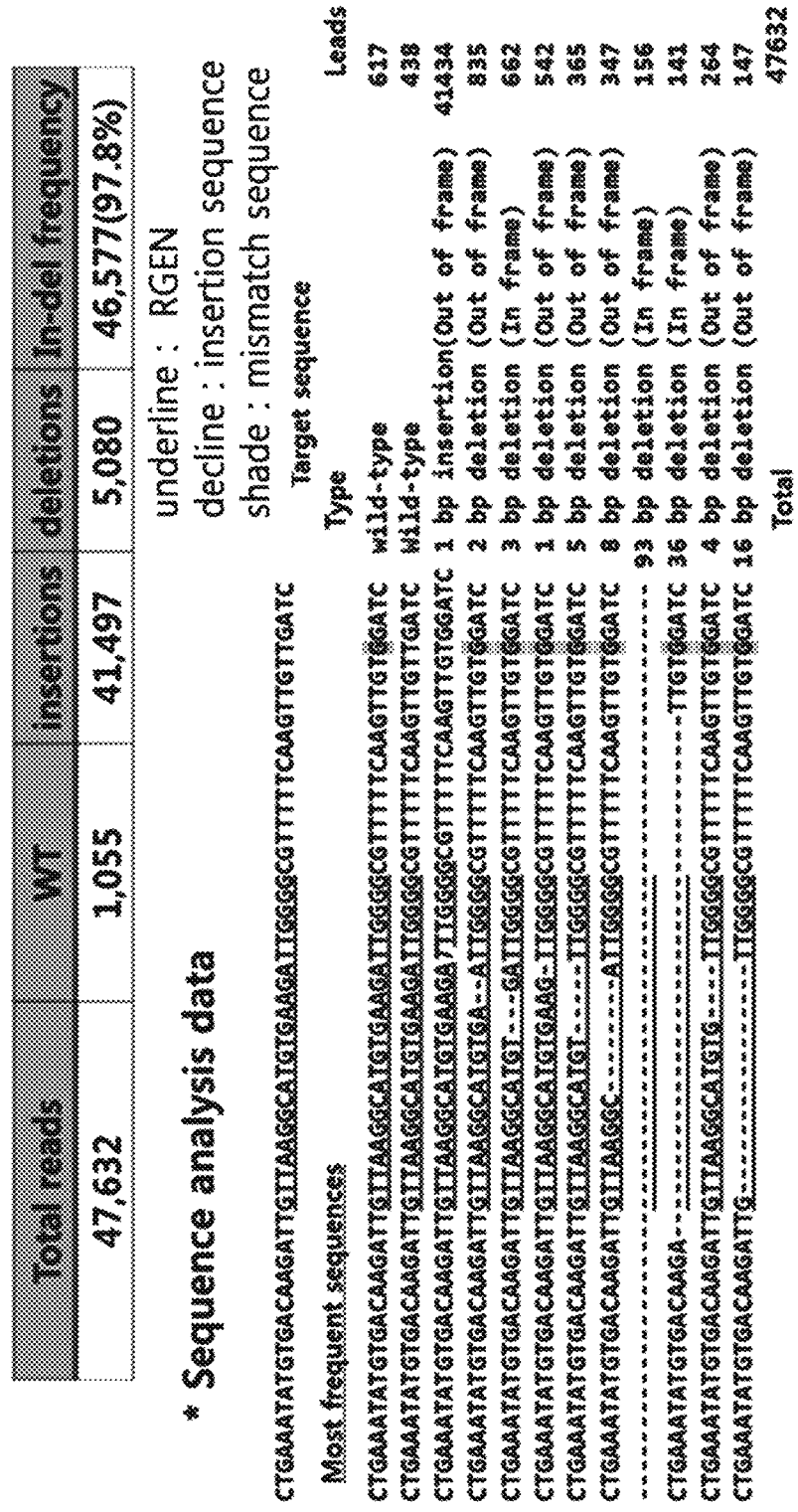

Additionally, to confirm whether the mutation of the nucleic acid caused a change at the amino acid level, FIG. 25 illustrates the results of aligning the amino acid sequences of the target sites of sgRNA2 derived from WT (named F3H_aWT and F3H_bWT, respectively) and mutations which are F3Ha and F3Hb (named F3H_aMutant and F3H_bMutant, respectively).

From these results, it could be seen that in a non-haemdioxygenase (DIOX_N) domain region in morphine synthesis N-terminal, many amino acid changes were made in the mutation type compared to WT. Therefore, it could be predicted that the change in the above region would ultimately result in the total or partial loss of F3H functionality as the enzyme activity decreased.

TABLE 5

| (T0) | Total count | Insertion | Deletion | InDel | Indel-ratio | Mutation Pattern | Genotype |
|---|---|---|---|---|---|---|---|
| Plant | | | | plant 1 | | | |
| allele_a | 7612 | 0 | 6 | 6 | 0.08% | — | Homozygous |
| allele_b | 5008 | 4 | 3 | 7 | 0.14% | — | Homozygous |
| Flower color | | | Purple violet (WT) | | | | |
| Plant | | | | plant 2 | | | |
| allele_a | 8770 | 8574 | 151 | 8725 | 99.49% | 1 bp ins | Homozygous |
| allele_b | 8003 | 14 | 7984 | 7998 | 99.94% | 2 bp del | Homozygous |
| Flower color | | | Purple spotted White (Mutant) | | | | |

In addition, the sequencing analysis results and indel results of F3Ha and F3Hb, which are gene sequences having an SNP in petunia, having undergone Agrobacterium-mediated transformation are illustrated in FIGS. 26 to 31 (each target gene is named 0324 L4-1, 0324 L9-1, and 0324 L9-2).

As a result, it could be confirmed that indel mutations were generated at a high ratio by the composition of the present application even in F3Ha and F3Hb having an SNP.

Through this result, it could be seen that not only the RNP-mediated transformation method previously performed but also the transformation method using Agrobacterium are effective.

Figure 32:
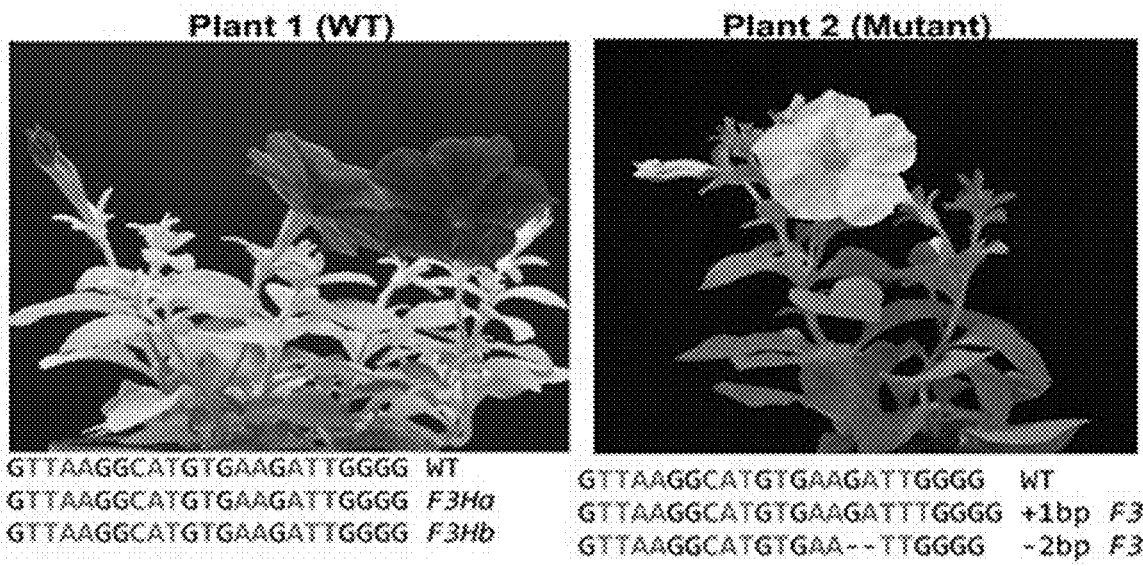
FIG. 32 is a view illustrating the flower colors of petunia plants in which wild-type F3H (named Plant 1) and mutant F3H (named Plant 2) have undergone agrobacterium-mediated transformation.

Meanwhile, the flower colors of the wild type and the mutant type petunias used in the present example were also compared and are illustrated in FIG. 32. As can be seen from FIG. 32, it can be seen that because the wild type (named Plant 1) is purple, but the mutant type (named Plant 2) is purple spotted white, the flower color of petunia is clearly changed.

The results showed that mutations could be effectively introduced into the F3H gene by the CRISPR/Cas9 composition of the present application, and as a result, it was shown that the F3H gene could be knocked out (KO) to reduce the expression thereof, thereby changing the flower color of petunias.

Industrial Applicability

The present application may provide a composition for editing a flavonoid biosynthetic gene using a CRISPR/Cas9 system, and a method for using the same.

Sequence Listing Free Text

It relates to a target sequence, a guide RNA sequence, and a primer sequence for editing flavonoid biosynthetic genes.

This application contains references to amino acid sequences and/or nucleic acid sequences which have been submitted herewith as the sequence listing text file. The aforementioned sequence listing is hereby incorporated by reference in its entirety pursuant to 37 C.F.R. § 1.52 (e).

What is claimed is:

1. A method of producing a genome-edited plant, wherein the plant is a petunia, the method comprising:
   introducing a composition into a plant cell
      wherein the composition comprises
         a Cas protein, or a nucleic acid sequence encoding the same, wherein the Cas protein is the *Streptococcus pyogenes*-derived Cas9 protein; and
         a guide RNA having a first portion complementary to about 20nt of a target sequence and a second portion capable of interacting with the Cas protein, or a nucleic acid sequence encoding the guide RNA,
      wherein the target sequence is a part of sequence of F3H gene on genomic DNA in a petunia and is selected from SEQ ID NOs: 2, 3, 4, and 5 of the F3H gene,
      wherein the guide RNA is selected from the group consisting of SEQ ID NO: 43, 44, 45, and 46, which is corresponding to the target sequence of SEQ ID NOS: 2, 3, 4, and 5, respectively,
   wherein the plant cell is a protoplast form, and the composition induces an indel by cleaving one or more sequences selected from SEQ ID NOs: 2, 3, 4, and 5 on the genomic sequencing encoding F3H in the plant cell,
   obtaining an engineered plant cell which comprises an artificial mutation on the genome of the plant cell, and
   regenerating the engineered plant cell to be the genome-edited plant,
   wherein the genome-edited plant has a changed color characteristic compared to a wild type thereof.

2. The method of claim 1, wherein the introducing is performed with one or more methods selected from electroporation, a gene gun method, sonoporation, magnetofection, a polyethylene glycol (PEG) method, an Agrobacterium method, transient cell compression or squeezing, lipid-mediated transfection and a nanoparticle method.

3. The method of claim 1, wherein the plant cell is derived from a root, a stem, a leaf, a flower or a seed.

4. The method of claim 1, wherein the step of regenerating the engineered plant cell to be the genome-edited plant comprises:
   forming a callus by culturing the engineered plant cell, and
   further culturing the callus to be the genome-edited plant.

* * * * *

SEQUENCE LISTING

```
<160> NUMBER OF SEQ ID NOS: 69

<210> SEQ ID NO 1
<211> LENGTH: 23
<212> TYPE: DNA
<213> ORGANISM: Petunia x hybrida

<400> SEQUENCE: 1
ttgggatctc attgctgaat tgg                                            23

<210> SEQ ID NO 2
<211> LENGTH: 23
<212> TYPE: DNA
<213> ORGANISM: Petunia x hybrida

<400> SEQUENCE: 2
gttaaggcat gtgaagattg ggg                                            23

<210> SEQ ID NO 3
<211> LENGTH: 23
<212> TYPE: DNA
<213> ORGANISM: Petunia x hybrida

<400> SEQUENCE: 3
ctgcggtttg acatgtctgg tgg                                            23

<210> SEQ ID NO 4
```

```
<211> LENGTH: 23
<212> TYPE: DNA
<213> ORGANISM: Petunia x hybrida

<400> SEQUENCE: 4
ggccagacaa accagaagga tgg                                          23

<210> SEQ ID NO 5
<211> LENGTH: 23
<212> TYPE: DNA
<213> ORGANISM: Petunia x hybrida

<400> SEQUENCE: 5
ttcagtccaa gggtaaggtc agg                                          23

<210> SEQ ID NO 6
<211> LENGTH: 21
<212> TYPE: DNA
<213> ORGANISM: Artificial Sequence
<220> FEATURE:
<223> OTHER INFORMATION: primer

<400> SEQUENCE: 6
ggcaccttca acattaacag c                                            21

<210> SEQ ID NO 7
<211> LENGTH: 20
<212> TYPE: DNA
<213> ORGANISM: Artificial Sequence
<220> FEATURE:
<223> OTHER INFORMATION: primer

<400> SEQUENCE: 7
aacgccccaa tcttcacatg                                              20

<210> SEQ ID NO 8
<211> LENGTH: 56
<212> TYPE: DNA
<213> ORGANISM: Artificial Sequence
<220> FEATURE:
<223> OTHER INFORMATION: primer

<400> SEQUENCE: 8
acactctttc cctacacgac gctcttccga tctgcacctt caacattaac agcatt      56

<210> SEQ ID NO 9
<211> LENGTH: 54
<212> TYPE: DNA
<213> ORGANISM: Artificial Sequence
<220> FEATURE:
<223> OTHER INFORMATION: primer

<400> SEQUENCE: 9
gtgactggag ttcagacgtg tgctcttccg atctccccaa tcttcacatg cctt        54

<210> SEQ ID NO 10
<211> LENGTH: 23
<212> TYPE: DNA
<213> ORGANISM: Artificial Sequence
<220> FEATURE:
<223> OTHER INFORMATION: primer

<400> SEQUENCE: 10
gcaccttcaa cattaacagc att                                          23
```

```
<210> SEQ ID NO 11
<211> LENGTH: 20
<212> TYPE: DNA
<213> ORGANISM: Artificial Sequence
<220> FEATURE:
<223> OTHER INFORMATION: primer

<400> SEQUENCE: 11
ccccaatctt cacatgcctt                                              20

<210> SEQ ID NO 12
<211> LENGTH: 22
<212> TYPE: DNA
<213> ORGANISM: Artificial Sequence
<220> FEATURE:
<223> OTHER INFORMATION: primer

<400> SEQUENCE: 12
gcttacaacc aattcagcaa tg                                           22

<210> SEQ ID NO 13
<211> LENGTH: 20
<212> TYPE: DNA
<213> ORGANISM: Artificial Sequence
<220> FEATURE:
<223> OTHER INFORMATION: primer

<400> SEQUENCE: 13
gtctggtggc aagaaaggtg                                              20

<210> SEQ ID NO 14
<211> LENGTH: 55
<212> TYPE: DNA
<213> ORGANISM: Artificial Sequence
<220> FEATURE:
<223> OTHER INFORMATION: primer

<400> SEQUENCE: 14
acactctttc cctacacgac gctcttccga tctccaattc agcaatgaga tccca        55

<210> SEQ ID NO 15
<211> LENGTH: 54
<212> TYPE: DNA
<213> ORGANISM: Artificial Sequence
<220> FEATURE:
<223> OTHER INFORMATION: primer

<400> SEQUENCE: 15
gtgactggag ttcagacgtg tgctcttccg atctacatgt caaaccgcag cttt         54

<210> SEQ ID NO 16
<211> LENGTH: 22
<212> TYPE: DNA
<213> ORGANISM: Artificial Sequence
<220> FEATURE:
<223> OTHER INFORMATION: primer

<400> SEQUENCE: 16
ccaattcagc aatgagatcc ca                                           22

<210> SEQ ID NO 17
<211> LENGTH: 20
<212> TYPE: DNA
<213> ORGANISM: Artificial Sequence
<220> FEATURE:
<223> OTHER INFORMATION: primer
```

```
<400> SEQUENCE: 17
acatgtcaaa ccgcagcttt                                                    20

<210> SEQ ID NO 18
<211> LENGTH: 20
<212> TYPE: DNA
<213> ORGANISM: Artificial Sequence
<220> FEATURE:
<223> OTHER INFORMATION: primer

<400> SEQUENCE: 18
aaggcatgtg aagattgggg                                                    20

<210> SEQ ID NO 19
<211> LENGTH: 22
<212> TYPE: DNA
<213> ORGANISM: Artificial Sequence
<220> FEATURE:
<223> OTHER INFORMATION: primer

<400> SEQUENCE: 19
gtcacttcac atttgtcttc cg                                                 22

<210> SEQ ID NO 20
<211> LENGTH: 53
<212> TYPE: DNA
<213> ORGANISM: Artificial Sequence
<220> FEATURE:
<223> OTHER INFORMATION: primer

<400> SEQUENCE: 20
acactctttc cctacacgac gctcttccga tctgttgtgg atcatggggt tga               53

<210> SEQ ID NO 21
<211> LENGTH: 57
<212> TYPE: DNA
<213> ORGANISM: Artificial Sequence
<220> FEATURE:
<223> OTHER INFORMATION: primer

<400> SEQUENCE: 21
gtgactggag ttcagacgtg tgctcttccg atctgcatgt tgaatactac ttggtcg           57

<210> SEQ ID NO 22
<211> LENGTH: 20
<212> TYPE: DNA
<213> ORGANISM: Artificial Sequence
<220> FEATURE:
<223> OTHER INFORMATION: primer

<400> SEQUENCE: 22
gttgtggatc atggggttga                                                    20

<210> SEQ ID NO 23
<211> LENGTH: 23
<212> TYPE: DNA
<213> ORGANISM: Artificial Sequence
<220> FEATURE:
<223> OTHER INFORMATION: primer

<400> SEQUENCE: 23
gcatgttgaa tactacttgg tcg                                                23

<210> SEQ ID NO 24
<211> LENGTH: 20
```

```
<212> TYPE: DNA
<213> ORGANISM: Artificial Sequence
<220> FEATURE:
<223> OTHER INFORMATION: primer

<400> SEQUENCE: 24
ggaacggtaa tggaagagca                                                    20

<210> SEQ ID NO 25
<211> LENGTH: 19
<212> TYPE: DNA
<213> ORGANISM: Artificial Sequence
<220> FEATURE:
<223> OTHER INFORMATION: primer

<400> SEQUENCE: 25
catgacggat agccaggaa                                                     19

<210> SEQ ID NO 26
<211> LENGTH: 55
<212> TYPE: DNA
<213> ORGANISM: Artificial Sequence
<220> FEATURE:
<223> OTHER INFORMATION: primer

<400> SEQUENCE: 26
acactctttc cctacacgac gctcttccga tcttgtgacc tactttctcgt accca            55

<210> SEQ ID NO 27
<211> LENGTH: 54
<212> TYPE: DNA
<213> ORGANISM: Artificial Sequence
<220> FEATURE:
<223> OTHER INFORMATION: primer

<400> SEQUENCE: 27
gtgactggag ttcagacgtg tgctcttccg atcttaccca aagtgtcctg agcc              54

<210> SEQ ID NO 28
<211> LENGTH: 22
<212> TYPE: DNA
<213> ORGANISM: Artificial Sequence
<220> FEATURE:
<223> OTHER INFORMATION: primer

<400> SEQUENCE: 28
tgtgacctac ttttcgtacc ca                                                 22

<210> SEQ ID NO 29
<211> LENGTH: 20
<212> TYPE: DNA
<213> ORGANISM: Artificial Sequence
<220> FEATURE:
<223> OTHER INFORMATION: primer

<400> SEQUENCE: 29
tacccaaagt gtcctgagcc                                                    20

<210> SEQ ID NO 30
<211> LENGTH: 19
<212> TYPE: DNA
<213> ORGANISM: Artificial Sequence
<220> FEATURE:
<223> OTHER INFORMATION: primer

<400> SEQUENCE: 30
```
agggtgaagt ggtccaaga 19

<210> SEQ ID NO 31
<211> LENGTH: 19
<212> TYPE: DNA
<213> ORGANISM: Artificial Sequence
<220> FEATURE:
<223> OTHER INFORMATION: primer

<400> SEQUENCE: 31
ttgaaccgtc cattgctca 19

<210> SEQ ID NO 32
<211> LENGTH: 53
<212> TYPE: DNA
<213> ORGANISM: Artificial Sequence
<220> FEATURE:
<223> OTHER INFORMATION: primer

<400> SEQUENCE: 32
acactctttc cctacacgac gctcttccga tctggcatgt gtggatatgg acc 53

<210> SEQ ID NO 33
<211> LENGTH: 54
<212> TYPE: DNA
<213> ORGANISM: Artificial Sequence
<220> FEATURE:
<223> OTHER INFORMATION: primer

<400> SEQUENCE: 33
gtgactggag ttcagacgtg tgctcttccg atctggctga acagtgatcc aagt 54

<210> SEQ ID NO 34
<211> LENGTH: 20
<212> TYPE: DNA
<213> ORGANISM: Artificial Sequence
<220> FEATURE:
<223> OTHER INFORMATION: primer

<400> SEQUENCE: 34
ggcatgtgtg gatatggacc 20

<210> SEQ ID NO 35
<211> LENGTH: 20
<212> TYPE: DNA
<213> ORGANISM: Artificial Sequence
<220> FEATURE:
<223> OTHER INFORMATION: primer

<400> SEQUENCE: 35
ggctgaacag tgatccaagt 20

<210> SEQ ID NO 36
<211> LENGTH: 2320
<212> TYPE: DNA
<213> ORGANISM: Petunia x hybrida

<400> SEQUENCE: 36
tctagaagga aagcacgtgc agtgttagtt gccacgagag gttgttagag ttccacgctt 60
acatgcaact cttactcctt tataaatctc agccccttac ttcccctaac tcctcactac 120
tttccaattt ccgcatatat atcaacccat acttgtccag taaaaagttc gtgtcactct 180
tactatttac atctttattt ttttcacaag aaggcttctc aaacaaagaa ggaaggttgt 240
aaatggcacc ttcaacatta acagcattag cagaagaaaa gaccccttcaa acaagtttca 300

-continued

```
ttagggatga agatgaacgt ccaaaagtgg cttacaacca attcagcaat gagatcccaa      360
ttatctcgtt agagggcatt gatgatgaaa ctggtaaaag agctgaaata tgtgacaaga      420
ttgttaaggc atgtgaagat tggggcgttt tcaagttgt ggatcatggg gttgatgctg       480
aacttatttc ccaaatgaca acttttgcta agaattctt tgcttttgcct cctgaggaaa      540 agctgcggtt tgacatgtct ggtggcaaga aggtggatt tattgtctct agccatctac       600
aggtaaatta accaatgcat gttgaatact acttggtcgt agcctaccgt ctcaaaaacc      660
gtaacgtgtc acttcacatt tgtcttccga gttaaagaca atttaagttg tgagattttt      720
tcacattatc atgttaagtt ccccgcaaac acgtaataaa gttatactat aatctgtaac      780
agcttaaata aaattaattt tgtggtacta tctctgtata ttagtcttaa atccttggaa      840
tatgtccaaa attaacgact ttaagctaat taaggatcgg caatgtaaaa aaataacac       900 gatttgggta cttataaggt aattgcatgt atttgcatgt tattttcatg ataagcatta      960
ataaaaacat gacacaaata atactgtcgt aactaacctg gtatcacatg gacataattt     1020
gagtccttaa tagtaatatt tatgagttgt aaatttaact ctctaggaaa ctctcatgta     1080
gatttagatt tcaggtattt cgcacaacaa tttagtaaat caatttgact tttagtatgt     1140
agaaggctat cagaaatatg aacggtaat ggaagagcat taaattgaca tgtactctgc      1200
taattattgt tcatgaatgc ctctgttttt aagggtgaag tggtccaaga ttggcgtgaa     1260
attgtgacct acttttcgta cccaacaagg gcaagagact actctagatg gccagacaaa     1320
ccagaaggat ggatagctgt gactcagaaa tatagtgaaa agttaatgga gttagcttgc     1380
aagttattgg atgtcctatc agaggctatg ggcttggaga aggaggcctt aaccaaggca     1440
tgtgtggata tggaccaaaa agtggttgtc aattttttacc caaagtgtcc tgagcctgac    1500
cttacccttg gactgaaaag acacactgat ccaggaacca tcactctctt gttacaagac     1560
caagttggtg ggcttcaagc tactaaagat aatggcaaaa cttggatcac tgttcagcct     1620
gttgaaggtg cttttgttgt caatcttggt gaccacggtc atgtaagttt cacaggtttt     1680
tacattgaag gattttttga aactaaattc ctggctatcc gtcatgattc tgatgattag     1740
cttttctgca aagggttttt aagggagtca aaagttatac aatggcactg gaatgtctta     1800
tttctcaaat caccctaagt tctattatga ccctacaatt gttttgtata ctatatttat     1860
gaacttagaa attgtcattc aattatgtga ttttggacag ttttttgagca atggacggtt    1920 caagaatgct gatcatcaag cagtggtgaa ctcaaatagc agcaggttat cgatagccac     1980
gtttcagaat ccggcaccag aggcgatagt gtatccattg aaaattaggg aaggagagaa     2040
gtcaataatg gatgagccca taacatttgc agaaatgtac agaaggaaaa tgagcaagga    2100
tttagaactt gctaggctca agaagcaggc caaggagcag cagttacaag ctgaagttgc    2160
tgctgagaag gctaagttgg agtccaagcc cattgaggaa attcttgctt aaattttaca    2220 tttttttagca tatttattat attatatgat gaaaaatgat cctcctacct actgttgtaa    2280
tatctgaatc ggtaataaag ttcccacacc tatatgtttg                           2320
```

<210> SEQ ID NO 37
<211> LENGTH: 23
<212> TYPE: DNA
<213> ORGANISM: Artificial Sequence
<220> FEATURE:
<223> OTHER INFORMATION: F3H 1 target site(2)

<400> SEQUENCE: 37
aaccctagag taacgactta acc                                        23

<210> SEQ ID NO 38
<211> LENGTH: 23
<212> TYPE: DNA
<213> ORGANISM: Artificial Sequence
<220> FEATURE:
<223> OTHER INFORMATION: F3H 2 target site(2)

<400> SEQUENCE: 38
caattccgta cacttctaac ccc                                        23

<210> SEQ ID NO 39
<211> LENGTH: 23
<212> TYPE: DNA
<213> ORGANISM: Artificial Sequence
<220> FEATURE:
<223> OTHER INFORMATION: F3H 3 target site(2)

<400> SEQUENCE: 39
gacgccaaac tgtacagacc acc                                        23

<210> SEQ ID NO 40
<211> LENGTH: 23
<212> TYPE: DNA
<213> ORGANISM: Artificial Sequence
<220> FEATURE:
<223> OTHER INFORMATION: F3H 4 target site(2)

<400> SEQUENCE: 40
ccggtctgtt tggtcttcct acc                                        23

<210> SEQ ID NO 41
<211> LENGTH: 23
<212> TYPE: DNA
<213> ORGANISM: Artificial Sequence
<220> FEATURE:
<223> OTHER INFORMATION: F3H 5 target site(2)

<400> SEQUENCE: 41
aagtcaggtt cccattccag tcc                                        23

<210> SEQ ID NO 42
<211> LENGTH: 20
<212> TYPE: RNA
<213> ORGANISM: Artificial Sequence
<220> FEATURE:
<223> OTHER INFORMATION: F3H 1 sgRNA(1)

<400> SEQUENCE: 42
uugggaucuc auugcugaau                                            20

<210> SEQ ID NO 43
<211> LENGTH: 20
<212> TYPE: RNA
<213> ORGANISM: Artificial Sequence
<220> FEATURE:
<223> OTHER INFORMATION: F3H 2 sgRNA(1)

<400> SEQUENCE: 43
guuaaggcau gugaagauug                                            20

<210> SEQ ID NO 44
<211> LENGTH: 20
<212> TYPE: RNA
<213> ORGANISM: Artificial Sequence

```
<220> FEATURE:
<223> OTHER INFORMATION: F3H 3 sgRNA(1)

<400> SEQUENCE: 44
cugcgguuug acaugucugg                                               20

<210> SEQ ID NO 45
<211> LENGTH: 20
<212> TYPE: RNA
<213> ORGANISM: Artificial Sequence
<220> FEATURE:
<223> OTHER INFORMATION: F3H 4 sgRNA(1)

<400> SEQUENCE: 45
ggccagacaa accagaagga                                               20

<210> SEQ ID NO 46
<211> LENGTH: 20
<212> TYPE: RNA
<213> ORGANISM: Artificial Sequence
<220> FEATURE:
<223> OTHER INFORMATION: F3H 5 sgRNA(1)

<400> SEQUENCE: 46
uucaguccaa ggguaagguc                                               20

<210> SEQ ID NO 47
<211> LENGTH: 20
<212> TYPE: RNA
<213> ORGANISM: Artificial Sequence
<220> FEATURE:
<223> OTHER INFORMATION: F3H 1 sgRNA(2)

<400> SEQUENCE: 47
aacccuagag uaacgacuua                                               20

<210> SEQ ID NO 48
<211> LENGTH: 20
<212> TYPE: RNA
<213> ORGANISM: Artificial Sequence
<220> FEATURE:
<223> OTHER INFORMATION: F3H 2 sgRNA(2)

<400> SEQUENCE: 48
caauuccgua cacuucuaac                                               20

<210> SEQ ID NO 49
<211> LENGTH: 20
<212> TYPE: RNA
<213> ORGANISM: Artificial Sequence
<220> FEATURE:
<223> OTHER INFORMATION: F3H 3 sgRNA(2)

<400> SEQUENCE: 49
gacgccaaac uguacagacc                                               20

<210> SEQ ID NO 50
<211> LENGTH: 20
<212> TYPE: RNA
<213> ORGANISM: Artificial Sequence
<220> FEATURE:
<223> OTHER INFORMATION: F3H 4 sgRNA(2)

<400> SEQUENCE: 50 ccgucuguu uggucuuccu                                                20
```

```
<210> SEQ ID NO 51
<211> LENGTH: 20
<212> TYPE: RNA
<213> ORGANISM: Artificial Sequence
<220> FEATURE:
<223> OTHER INFORMATION: F3H 5 sgRNA(2)

<400> SEQUENCE: 51
aagucagguu cccauuccag                                                  20

<210> SEQ ID NO 52
<211> LENGTH: 248
<212> TYPE: DNA
<213> ORGANISM: Artificial Sequence
<220> FEATURE:
<223> OTHER INFORMATION: F3H-A

<400> SEQUENCE: 52
ggcttacaac caattcagca atgagatccc aattatctcg ttagagggca ttgatgatga      60
aactggtaaa agagctgaaa tatgtgacaa gattgttaag gcatgtgaag attggggcgt    120
ttttcaagtt gtggatcatg ggttgatgc tgaacttatt cccaaatga caacttttgc      180 taaagaattc tttgctttgc ctcctgagga aaagctgcgg tttgacatgt ctggtggcaa    240
gaaaggtg                                                             248

<210> SEQ ID NO 53
<211> LENGTH: 248
<212> TYPE: DNA
<213> ORGANISM: Artificial Sequence
<220> FEATURE:
<223> OTHER INFORMATION: F3H-B

<400> SEQUENCE: 53
tgcttacaac caattcagca atgagatacc aattatctcg ttagagggta ttgatgatga      60
aactggtaaa agagctgaaa tatgtgacaa gattgttaag gcatgtgaag attggggcgt    120
ttttcaagtt gttgatcatg ggttgatgc tgaacttatt cccaaatga caactcttgc      180 taaagaattc tttgctttgc ctcctgagga aaagctacgg tttgacatgt ctggtggcaa    240
gaaaggtg                                                             248

<210> SEQ ID NO 54
<211> LENGTH: 23
<212> TYPE: DNA
<213> ORGANISM: Artificial Sequence
<220> FEATURE:
<223> OTHER INFORMATION: F3H-A target site(1)

<400> SEQUENCE: 54
gttaaggcat gtgaagattg ggg                                              23

<210> SEQ ID NO 55
<211> LENGTH: 23
<212> TYPE: DNA
<213> ORGANISM: Artificial Sequence
<220> FEATURE:
<223> OTHER INFORMATION: F3H-B target site(1)

<400> SEQUENCE: 55
gttaaggcat gtgaagattg ggg                                              23

<210> SEQ ID NO 56
<211> LENGTH: 20
```

```
<212> TYPE: RNA
<213> ORGANISM: Artificial Sequence
<220> FEATURE:
<223> OTHER INFORMATION: F3H-A sgRNA (1)

<400> SEQUENCE: 56
guuaaggcau gugaagauug                                                    20

<210> SEQ ID NO 57
<211> LENGTH: 20
<212> TYPE: RNA
<213> ORGANISM: Artificial Sequence
<220> FEATURE:
<223> OTHER INFORMATION: F3H-B sgRNA (1)

<400> SEQUENCE: 57
guuaaggcau gugaagauug                                                    20

<210> SEQ ID NO 58
<211> LENGTH: 23
<212> TYPE: DNA
<213> ORGANISM: Artificial Sequence
<220> FEATURE:
<223> OTHER INFORMATION: F3H-A target site(2)

<400> SEQUENCE: 58
caattccgta cacttctaac ccc                                                23

<210> SEQ ID NO 59
<211> LENGTH: 23
<212> TYPE: DNA
<213> ORGANISM: Artificial Sequence
<220> FEATURE:
<223> OTHER INFORMATION: F3H-B target site(2)

<400> SEQUENCE: 59
caattccgta cacttctaac ccc                                                23

<210> SEQ ID NO 60
<211> LENGTH: 20
<212> TYPE: RNA
<213> ORGANISM: Artificial Sequence
<220> FEATURE:
<223> OTHER INFORMATION: F3H-A sgRNA (2)

<400> SEQUENCE: 60
caauuccgua cacuucuaac                                                    20

<210> SEQ ID NO 61
<211> LENGTH: 20
<212> TYPE: RNA
<213> ORGANISM: Artificial Sequence
<220> FEATURE:
<223> OTHER INFORMATION: F3H-B sgRNA (2)

<400> SEQUENCE: 61
caauuccgua cacuucuaac                                                    20

<210> SEQ ID NO 62
<211> LENGTH: 23
<212> TYPE: DNA
<213> ORGANISM: Artificial Sequence
<220> FEATURE:
<223> OTHER INFORMATION: F3H-A PCR primer(F)

<400> SEQUENCE: 62
```

```
ggcttacaac caattcagca atg                                          23

<210> SEQ ID NO 63
<211> LENGTH: 23
<212> TYPE: DNA
<213> ORGANISM: Artificial Sequence
<220> FEATURE:
<223> OTHER INFORMATION: F3H-A PCR primer(R)

<400> SEQUENCE: 63
ggcttacaac caattcagca atg                                          23

<210> SEQ ID NO 64
<211> LENGTH: 22
<212> TYPE: DNA
<213> ORGANISM: Artificial Sequence
<220> FEATURE:
<223> OTHER INFORMATION: F3H-A Adapt PCR primer(F)

<400> SEQUENCE: 64
ccaattcagc aatgagatcc ca                                           22

<210> SEQ ID NO 65
<211> LENGTH: 20
<212> TYPE: DNA
<213> ORGANISM: Artificial Sequence
<220> FEATURE:
<223> OTHER INFORMATION: F3H-A Adapt PCR primer(R)

<400> SEQUENCE: 65
acatgtcaaa ccgcagcttt                                              20

<210> SEQ ID NO 66
<211> LENGTH: 23
<212> TYPE: DNA
<213> ORGANISM: Artificial Sequence
<220> FEATURE:
<223> OTHER INFORMATION: F3H-B PCR primer(F)

<400> SEQUENCE: 66
ggcttacaac caattcagca atg                                          23

<210> SEQ ID NO 67
<211> LENGTH: 20
<212> TYPE: DNA
<213> ORGANISM: Artificial Sequence
<220> FEATURE:
<223> OTHER INFORMATION: F3H-B PCR primer(R)

<400> SEQUENCE: 67
cacctttctt gccaccagac                                              20

<210> SEQ ID NO 68
<211> LENGTH: 22
<212> TYPE: DNA
<213> ORGANISM: Artificial Sequence
<220> FEATURE:
<223> OTHER INFORMATION: F3H-B Adapt PCR primer(F)

<400> SEQUENCE: 68
ccaattcagc aatgagatcc ca                                           22

<210> SEQ ID NO 69
<211> LENGTH: 20
<212> TYPE: DNA
<213> ORGANISM: Artificial Sequence
```

```
<220> FEATURE:
<223> OTHER INFORMATION: F3H-B Adapt PCR primer(R)

<400> SEQUENCE: 69
acatgtcaaa ccgcagcttt                                               20
```